United States Patent [19]
De Robertis et al.

[11] Patent Number: 5,679,783
[45] Date of Patent: Oct. 21, 1997

[54] DNA ENCODING A TISSUE DIFFERENTIATION AFFECTING FACTOR

[75] Inventors: Edward M. De Robertis, Pacific Palisades; Yoshiki Sasai, Los Angeles, both of Calif.

[73] Assignee: The Regents of the University of California, Oakland, Calif.

[21] Appl. No.: 343,760

[22] Filed: Nov. 22, 1994

[51] Int. Cl.$^6$ .................... C12N 15/12; C07K 14/46
[52] U.S. Cl. ............... 536/23.5; 435/69.1; 435/172.3; 435/252.3; 435/320.1; 935/11; 935/22; 935/66; 530/350
[58] Field of Search .................... 536/23.1, 23.5; 435/69.1, 172.3, 252.3, 320.1; 514/44; 935/11, 22, 27, 29, 31, 32, 66; 530/350

[56] References Cited

U.S. PATENT DOCUMENTS 5,229,500  7/1993  Barde et al. .................... 530/399

FOREIGN PATENT DOCUMENTS

93/09229  5/1993  WIPO .
94/05791  3/1994  WIPO .
94/05800  3/1994  WIPO .

OTHER PUBLICATIONS

Sasai et al (1994) *Cell*, vol. 79, pp. 779–790.
Hawley (1981) The Condensed chemical dictionary, Van Nostrand Reinhold Company, 10th edition, p. 759.
Wahl, Stern and Stark, "Efficient Transfer of Large DNA Fragments from Agarose Gels to Diazobenzyloxymethyl-paper and Rapid Hybridization by Using Dextran Sulfate", *Proc. Natl. Acad. Sci. USA*, vol. 76, No. 8, pp. 3683–3687, Aug. 1979.
Urlaub and Chasin, "Isolation of Chinese Hamster Cell Mutants Deficient in Dihydrofolate Reductase Activity" *Proc. Natl. Acad. Sci. USA*, vol. 77, No. 7, pp. 4216–4220, Jul. 1980.
Hunt and Barker, "Von Willebrand Factor Shares a Distinctive Cysteine–Rich Domain with Thrombospondin and Procollagen", *Biochemical and Biophysical Research Communications*, vol. 144, No. 2, pp. 876–882, Apr. 29, 1987.
Kao and Elinson, "The Entire Mesodermal Mantle Behaves as Spemann's Organizer in Dorsoanterior Enhanced *Xenopus Laevis* Embryos", *Developmental Biology*, vol. 127, pp. 64–77, 1988.
Simmons, Levy, Yannoni and Erikson, "Identification of a Phorbol Ester–Repressible V–Src–Inducible Gene", *Proc. Natl. Acad. Sci. USA*, vol. 86, pp. 1178–1182, Feb. 1989.
Sokol, Wong and Melton, "A Mouse Macrophage Factor Induces Head Structures and Organizes a Body Axis in Xenopus", *Science*, vol. 249, pp. 561–564, Aug. 3, 1990.
Blumberg, Wright, De Robertis and Cho, "Organizer–Specific Homeobox Genes in *Xenopus Laevis* Embryos", *Science*, vol. 253, pp. 194–196, Jul. 12, 1991.

Amaya, Musci and Kirschner, "Expression of a Dominant Negative Mutant of the FGF Receptor Disrupts Mesoderm Formation in Xenopus Embryos", *Cell*, vol. 66, pp. 257–270, Jul. 26, 1991.
Smith and Harland, "Injected Xwnt–8 RNA Acts Early in Xenopus Embryos to Promote Formation of a Vegetal Dorsalizing Center", *Cell*, vol. 67, pp. 753–765, Nov. 15, 1991.
Ferguson and Anderson, "Localized Enhancement and Repression of the Activity of the TGF–β Family Member, Decapentaplegic, is Necessary for Dorsal–Ventral Pattern Formation in the Drosophila Embryo", *Development*, vol. 114, pp. 583–597, 1992.
Schonbaum, Organ, Qu and Cavener, "The *Drosophila Melanogaster Stranded at Second* (sas) Gene Encodes a Putative Epidermal Cell Surface Receptor Required for Larval Development", *Developmental Biology*, vol. 151, pp. 431–445 (1992).
Jones, Lyons, Lapan, Wright and Hogan, "DVR–4 (Bone Morphogenetic Protein–4) as a Posterior–Ventralizing Factor in *Xenopus Mesoderm* Induction", *Development*, vol. 115, pp. 639–647, 1992.
Smith and Harland, "Expression Cloning of Noggin a New Dorsalizing Factor Localized to the Spemann Organizer in Xenopus Embryos", *Cell*, vol. 70, pp. 829–840, Sep. 4, 1992.
Fainsod, Steinbeisser and De Robertis, "On the Function of BMP–4 in Patterning the Marginal Zone of the Xenopus Embryo", *The EMBO Journal*, vol. 13, No. 21, pp. 5015–5025, 1994.
François, Solloway, O'Neill, Emery and Bier, "Dorsal–Ventral Patterning of the Drosophila Embryo Depends on a Putative Negative Growth Factor Encoded by the Short Gastrulation Gene", *Genes & Development*, vol. 8, pp. 2602–2616, 1994.
Hemmati–Brivanlou, Kelly and Melton, "Follistatin, an Antagonist of Activin, is Expressed in the Spemann Organizer and Displays Direct Neuralizing Activity", *Cell*, vol. 77, pp. 283–295, Apr. 22, 1994.
Graff, Thies, Song, Celeste and Melton, "Studies with a Xenopus BMP Receptor Suggest that Ventral Mesoderm–Inducing Signals Override Dorsal Signals in Vivo", *Cell*, vol. 79, pp. 169–179, Oct. 7, 1994.

*Primary Examiner*—John Ulm
*Assistant Examiner*—Prema Mertz
*Attorney, Agent, or Firm*—Majestic, Parsons, Siebert & Hsue

[57] ABSTRACT

A functional polypeptide designated "chordin" is described that is capable of inducing dorsal (and neural tissue) development in vertebrates, and which appears to be a secreted protein. There are substantial regions of conservation with Xenopus chordin with mouse chordin, and the human gene should also be similar in those regions. A full length Xenopus cDNA for chordin is illustrated by FIGS. 1A–1F, and contains a reading frame encoding a 941 residue, 105 kDa precursor protein.

8 Claims, 12 Drawing Sheets

| | | | | | |
|---|---|---|---|---|---|
| AGAAGTGTCC | CCTCCGGACA | TTGGTACCTG | CTGTGAAGAA | GAGGCTGGCC | 50 |
| TCTTCACAGG | GGAGGCCTGT | AACCATGGAC | GACACTTCTT | CTCCGACCGG | |
| CGGGTAGCAG | GGAGCGCTCT | CTGCACTATT | GGAGTGTGTG | TGGTGCAAAG | 100 |
| GCCCATCGTC | CCTCGCGAGA | GACGTGATAA | CCTCACACAC | ACCACGTTTC | |
| TGTGTGTACA | GAGCAACAAC | CCATGTACTG | GGAATGTGAG | CCAGAGAGCC | 150 |
| ACACACATGT | CTCGTTGTTG | GGTACATGAC | CCTTACACTC | GGTCTCTCGG | |
| AGAGACAAGT | AGCATAGTAG | TCGCTGAGAA | GGTGGCAAAG | TGACTGGCAC | 200 |
| TCTCTGTTCA | TCGTATCATC | AGCGACTCTT | CCACCGTTTC | ACTGACCGTG | |
| AGGCAGACTG | AAGGCTCATG | GTCCATAGAA | GAGTATAGTA | CAAAGCACAG | 250 |
| TCCGTCTGAC | TTCCGAGTAC | CAGGTATCTT | CTCATATCAT | GTTTCGTGTC | |
| ACATTGTACG | CTCACTATAC | GAGACAGAAC | GTTTGGAACC | ACAAAAATGC | 300 |
| TGTAACATGC | GAGTGATATG | CTCTGTCTTG | CAAACCTTGG | TGTTTTTACG | |
| AGTGTCCCCC | CATCCTACTT | GTGTGGACCC | TGTGGATTAT | GGCTGTGGAT | 350 |
| TCACAGGGGG | GTAGGATGAA | CACACCTGGG | ACACCTAATA | CCGACACCTA | |
| TGCTCTCGCC | CAAAGGTTTT | CTTGCCCATT | CAGCCTGAAC | AGGAGCCCCT | 400 |
| ACGAGAGCGG | GTTTCCAAAA | GAACGGGTAA | GTCGGACTTG | TCCTCGGGGA | |
| CCAATCCAAG | ACTCCAGCAG | GTTGTACATT | TGGTGGGAAA | TTTTACTCCC | 450 |
| GGTTAGGTTC | TGAGGTCGTC | CAACATGTAA | ACCACCCTTT | AAAATGAGGG | |
| TGGAGGATTC | ATGGCATCCA | GATCTTGGGG | AACCATTCGG | AGTTATGCAC | 500 |
| ACCTCCTAAG | TACCGTAGGT | CTAGAACCCC | TTGGTAAGCC | TCAATACGTG | |
| TGCGTACTAT | GCTATTGTGA | GCCGCAGCGA | AGTCGTCGGG | GAAAACCATC | 550 |
| ACGCATGATA | CGATAACACT | CGGCGTCGCT | TCAGCAGCCC | CTTTTGGTAG | |
| TGGTAAAGTC | AGCTGCAAAA | ACATCAAACA | TGATTGCCCC | TCACCCTCCT | 600 |
| ACCATTTCAG | TCGACGTTTT | TGTAGTTTGT | ACTAACGGGG | AGTGGGAGGA | |
| GTGCTAACCC | TATACTGCTC | CCATTACATT | GCTGCAAGAC | TTGTCCCAAA | 650 |
| CACGATTGGG | ATATGACGAG | GGTAATGTAA | CGACGTTCTG | AACAGGGTTT | |
| GCTCCTCCTC | CTCCTATAAA | GAAATCAGAC | TTTGTTTTTG | ACGGATTTGA | 700 |
| CGAGGAGGAG | GAGGATATTT | CTTTAGTCTG | AAACAAAAAC | TGCCTAAACT | |

Fig._1A

| | | | | | |
|---|---|---|---|---|---|
| GTATTTTCAA | GAGAAGGATG | ATGATCTTTA | TAATGATCGC | TCTTATCTGA | 750 |
| CATAAAAGTT | CTCTTCCTAC | TACTAGAAAT | ATTACTAGCG | AGAATAGACT | |
| GTTCTGATGA | TGTCGCTGTG | GAGGAGAGTC | GTTCAGAATA | TGTGGCACTA | 800 |
| CAAGACTACT | ACAGCGACAC | CTCCTCTCAG | CAAGTCTTAT | ACACCGTGAT | |
| CTAACAGCAC | CCAGCCATGT | GTGGCCCCA | GTTACCAGTG | GAGTAGCCAA | 850 |
| GATTGTCGTG | GGTCGGTACA | CACCGGGGT | CAATGGTCAC | CTCATCGGTT | |
| GGCTAGATTC | AACCTGCAGC | GCTCCAATTT | GCTCTTCTCA | ATCACTTATA | 900 |
| CCGATCTAAG | TTGGACGTCG | CGAGGTTAAA | CGAGAAGAGT | TAGTGAATAT | |
| AATGGATAGA | CAGACTTTCC | AGAATCCGTT | TCTCCGATCT | TGACGGTTCT | 950 |
| TTACCTATCT | GTCTGAAAGG | TCTTAGGCAA | AGAGGCTAGA | ACTGCCAAGA | |
| GTGCTGTTTG | AACACCCAGT | GCACAGAATG | GGATCCCCAC | GGGATGACAC | 1000 |
| CACGACAAAC | TTGTGGGTCA | CGTGTCTTAC | CCTAGGGGTG | CCCTACTGTG | |
| TATCTGTGGC | ATTTGGAGGT | CCCTTAATCG | GTCCACTCTA | CGTCTTCTCC | 1050 |
| ATAGACACCG | TAAACCTCCA | GGGAATTAGC | CAGGTGAGAT | GCAGAAGAGG | |
| GAATGGGTCA | CATTCTTGTA | TCTCTGGTGA | CCACAACACT | TTCAGAGCCG | 1100 |
| CTTACCCAGT | GTAAGAACAT | AGAGACCACT | GGTGTTGTGA | AAGTCTCGGC | |
| GAAATATCAG | GCAAGATTGT | CAAACACAAA | GCCCTATTTT | CAGAGTCCTT | 1150 |
| CTTTATAGTC | CGTTCTAACA | GTTTGTGTTT | CGGGATAAAA | GTCTCAGGAA | |
| CAGTGCACTT | CTTACCCCAG | AAGACTCTGA | TGAAACAGGA | GGTGGAGGAC | 1200 |
| GTCACGTGAA | GAATGGGGTC | TTCTGAGACT | ACTTTGTCCT | CCACCTCCTG | |
| TCGCAATGCT | AACACTGAGT | GATGTGGATG | ACAATCTGCA | CTTTATACTT | 1250 |
| AGCGTTACGA | TTGTGACTCA | CTACACCTAC | TGTTAGACGT | GAAATATGAA | |
| ATGCTCAGAG | GTCTAAGTGG | TGAAGAAGGA | GATCAGATTC | CAATACTTGT | 1300 |
| TACGAGTCTC | CAGATTCACC | ACTTCTTCCT | CTAGTCTAAG | GTTATGAACA | |
| GCAAATCTCA | CATCAGAACC | ATGTGATACG | GGAGCTATAT | GCCAACATCT | 1350 |
| CGTTTAGAGT | GTAGTCTTGG | TACACTATGC | CCTCGATATA | CGGTTGTAGA | |
| CTGCACAGGA | ACAAGACTTT | GCAGAGGTAT | TGCCAGACCT | TTCCAGTCGA | 1400 |
| GACGTGTCCT | TGTTCTGAAA | CGTCTCCATA | ACGGTCTGGA | AAGGTCAGCT | |

Fig._1B

| | | | | | |
|---|---|---|---|---|---|
| GAAATGCTGT | GGCTGGCGCA | AGGTCAGCTG | GAGATTTCAG | TGCAGACAGA | 1450 |
| CTTTACGACA | CCGACCGCGT | TCCAGTCGAC | CTCTAAAGTC | ACGTCTGTCT | |
| AGGGAGACGT | CCGCAAAGCA | TGTCAGGCAT | AATCACAGTC | AGAAAATCAT | 1500 |
| GCCCTCTGCA | GGCGTTTCGT | ACAGTCCGTA | TTAGTGTCAG | TCTTTTAGTA | |
| GTGACACTTT | GCAGAGTGTG | TTATCGGGTG | GTGACGCTTT | AAATCCCACC | 1550 |
| CACTGTGAAA | CGTCTCACAC | AATAGCCCAC | CACTGCGAAA | TTTAGGGTGG | |
| AAAACTGGAG | CCGTGGGATC | TGCAAGCATC | ACACTTCATG | AAAATGGAAC | 1600 |
| TTTTGACCTC | GGCACCCTAG | ACGTTCGTAG | TGTGAAGTAC | TTTTACCTTG | |
| TCTGGAATAT | CAGATTCAAA | TTGCTGGTAC | AATGAGTACT | GTGACAGCTG | 1650 |
| AGACCTTATA | GTCTAAGTTT | AACGACCATG | TTACTCATGA | CACTGTCGAC | |
| TGACACTGGA | GACAAAACCT | CGCCGAAAAA | CAAAGAGAAA | TATTCTGCAC | 1700 |
| ACTGTGACCT | CTGTTTTGGA | GCGGCTTTTT | GTTTCTCTTT | ATAAGACGTG | |
| GATATGAGCA | AGGACTACCA | TGATGGAAGG | GTCTGGGGAT | ATTGGATAGA | 1750 |
| CTATACTCGT | TCCTGATGGT | ACTACCTTCC | CAGACCCCTA | TAACCTATCT | |
| TGCTAATGCC | CGAGACCTAC | ATATGCTGTT | ACAAAGTGAG | CTCTTCCTCA | 1800 |
| ACGATTACGG | GCTCTGGATG | TATACGACAA | TGTTTCACTC | GAGAAGGAGT | |
| ATGTAGCGAC | AAAGGACTTC | CAGGAAGGGG | AACTCAGGGG | ACAAATAACC | 1850 |
| TACATCGCTG | TTTCCTGAAG | GTCCTTCCCC | TTGAGTCCCC | TGTTTATTGG | |
| CCTCTGCTAT | ACAGTGGCCT | GTGGGCCAGA | TATGAGAAGC | TCCCAGTTCC | 1900 |
| GGAGACGATA | TGTCACCGGA | CACCCGGTCT | ATACTCTTCG | AGGGTCAAGG | |
| TCTAGCTGGT | CAGTTTGTGT | CACCTCCCAT | CAGGACAGGT | TCAGCAGGTC | 1950 |
| AGATCGACCA | GTCAAACACA | GTGGAGGGTA | GTCCTGTCCA | AGTCGTCCAG | |
| ATGCATGGGT | TTCACTGGAT | GAGCACTGCC | ACCTGCATTA | TCAGATTGTG | 2000 |
| TACGTACCCA | AAGTGACCTA | CTCGTGACGG | TGGACGTAAT | AGTCTAACAC | |
| GTGACTGGTC | TGGGTAAGGC | AGAAGATGCT | GCACTGAACG | CACATCTACA | 2050 |
| CACTGACCAG | ACCCATTCCG | TCTTCTACGA | CGTGACTTGC | GTGTAGATGT | |
| TGGTTTTGCT | GAGCTTGGAG | AGGTCGGTGA | GAGCTCTCCT | GGACACAAGA | 2100 |
| ACCAAAACGA | CTCGAACCTC | TCCAGCCACT | CTCGAGAGGA | CCTGTGTTCT | |

Fig._1C

```
GGTTGTTAAA  GGGCTTCTAT  GGGTCAGAGG  CACAGGGTAG  TGTAAAAGAC    2150
CCAACAATTT  CCCGAAGATA  CCCAGTCTCC  GTGTCCCATC  ACATTTTCTG

CTTGACCTTG  AACTATTGGG  ACATCTGAGC  CGGGGCACAG  CATTTATTCA    2200
GAACTGGAAC  TTGATAACCC  TGTAGACTCG  GCCCCGTGTC  GTAAATAAGT

AGTGAGCACC  AAACTGAATC  CTCGTGGGGA  AATTCGAGGA  CAGATACACA    2250
TCACTCGTGG  TTTGACTTAG  GAGCACCCCT  TTAAGCTCCT  GTCTATGTGT

TACCTAACAG  CTGTGAATCT  GGAGGAGTTT  CTCTAACCCC  TGAAGAGCCT    2300
ATGGATTGTC  GACACTTAGA  CCTCCTCAAA  GAGATTGGGG  ACTTCTCGGA

GAGTATGAAT  ATGAAATATA  TGAGGAGGGA  AGGCAGCGCG  ACCCTGACGA    2350
CTCATACTTA  TACTTTATAT  ACTCCTCCCT  TCCGTCGCGC  TGGGACTGCT

TCTTCGGAAA  GACCCCAGAG  CATGCTCTTT  CGAAGGTCAA  CTAAGGGCCC    2400
AGAAGCCTTT  CTGGGGTCTC  GTACGAGAAA  GCTTCCAGTT  GATTCCCGGG

ATGGTTCACG  ATGGGCTCCA  GACTATGACA  GGAAATGCTC  TGTGTGCAGC    2450
TACCAAGTGC  TACCCGAGGT  CTGATACTGT  CCTTTACGAG  ACACACGTCG

TGTCAGAAGC  GTACCGTGAT  TTGTGATCCT  ATTGTGTGCC  CACCTCTGAA    2500
ACAGTCTTCG  CATGGCACTA  AACACTAGGA  TAACACACGG  GTGGAGACTT

CTGCTCCCAG  CCTGTCCATT  TGCCAGATCA  GTGCTGTCCT  GTGTGTGAAG    2550
GACGAGGGTC  GGACAGGTAA  ACGGTCTAGT  CACGACAGGA  CACACACTTC

AAAAAAAGA   AATGAGAGAG  GTGAAAAAAC  CAGAGAGGGC  TCGCACAAGT    2600
TTTTTTTCT   TTACTCTCTC  CACTTTTTTG  TGTCTCCCG   AGCGTGTTCA

GAAGGCTGCT  TTTTTGATGG  AGATCGCTCA  TGGAAGGCAG  CTGGTACACG    2650
CTTCCGACGA  AAAAACTACC  TCTAGCGAGT  ACCTTCCGTC  GACCATGTGC

TTGGCATCCT  TTTGTTCCTC  CATTTGGTCT  AATTAAATGT  GCCATTTGCA    2700
AACCGTAGGA  AAACAAGGAG  GTAAACCAGA  TTAATTTACA  CGGTAAACGT

CCTGCAAGGG  TTCCACTGGA  GAAGTGCACT  GTGAGAAGGT  GACCTGTCCA    2750
GGACGTTCCC  AAGGTGACCT  CTTCACGTGA  CACTCTTCCA  CTGGACAGGT

AAACTTTCCT  GTACCAACCC  AATCCGTGCC  AATCCTTCTG  ATTGCTGCAA    2800
TTTGAAAGGA  CATGGTTGGG  TTAGGCACGG  TTAGGAAGAC  TAACGACGTT
```

Fig._1D

```
GCAGTGCCCA  GTAGAGGAGC  GGAGTCCTAT  GGAACTGGCA  GACAGTATGC     2850
CGTCACGGGT  CATCTCCTCG  CCTCAGGATA  CCTTGACCGT  CTGTCATACG

AGTCAGATGG  AGCAGGATCA  TGCAGATTTG  GGCGTCACTG  GTACCCAAAT     2900
TCAGTCTACC  TCGTCCTAGT  ACGTCTAAAC  CCGCAGTGAC  CATGGGTTTA

CATGAGCGTT  GGCATCCAAC  TGTGCCACCC  TTTGGAGAGA  TGAAATGTGT     2950
GTACTCGCAA  CCGTAGGTTG  ACACGGTGGG  AAACCTCTCT  ACTTTACACA

TACATGCACT  TGTGCGGAGG  GCATTACACA  GTGTCGGAGA  CAGGAGTGTA     3000
ATGTACGTGA  ACACGCCTCC  CGTAATGTGT  CACAGCCTCT  GTCCTCACAT

CAGGAACTAC  ATGTGGTACT  GGTTCAAAGC  GGGACAGATG  TTGCACCAAG     3050
GTCCTTGATG  TACACCATGA  CCAAGTTTCG  CCCTGTCTAC  AACGTGGTTC

TGCAAAGATG  CCAATCAAGA  TGAAGATGAA  AAAGTGAAAT  CAGACGAGAC     3100
ACGTTTCTAC  GGTTAGTTCT  ACTTCTACTT  TTTCACTTTA  GTCTGCTCTG

AAGGACTCCA  TGGAGTTTTT  AGAGAGGAGA  GCAACTCGGG  CAATGGGACT     3150
TTCCTGAGGT  ACCTCAAAAA  TCTCTCCTCT  CGTTGAGCCC  GTTACCCTGA

GATTATCTAG  GCTCACAAAA  ACATGTCCCA  AGCTGAGACA  ACTGCCAGGA     3200
CTAATAGATC  CGAGTGTTTT  TGTACAGGGT  TCGACTCTGT  TGACGGTCCT

CTGGATGGTC  TGCACAATGT  TTTGTTCCAC  TCTGATAACA  CTGCTACTGG     3250
GACCTACCAG  ACGTGTTACA  AAACAAGGTG  AGACTATTGT  GACGATGACC

ATTTTACAGT  ATTTCCATTT  GTTTCATTTG  CTGCCATGAA  GCAGTGGGAT     3300
TAAAATGTCA  TAAAGGTAAA  CAAAGTAAAC  GACGGTACTT  CGTCACCCTA

TCTGGAGGCA  GCATTTGGAA  CTAAAATACC  TTGCCACCTT  GGATTCATCC     3350
AGACCTCCGT  CGTAAACCTT  GATTTTATGG  AACGGTGGAA  CCTAAGTAGG

CTTCCAACAC  CAAGTCAGTC  TTTCTGACAG  AAGCAACTCT  AAATCCTGCC     3400
GAAGGTTGTG  GTTCAGTCAG  AAAGACTGTC  TTCGTTGAGA  TTTAGGACGG

TAAACAGGAC  CCGGAGTTTT  AACGTCTGAT  CTGTAGAGTT  TCGCAACAGG     3450
ATTTGTCCTG  GGCCTCAAAA  TTGCAGACTA  GACATCTCAA  AGCGTTGTCC

AGCACAGACA  CAGCATAGGC  AGCTGTGCAT  ATGTAGATAT  ACTGACTAAA     3500
TCGTGTCTGT  GTCGTATCCG  TCGACACGTA  TACATCTATA  TGACTGATTT
```

Fig._1E

| | | | | | |
|---|---|---|---|---|---|
| CGTGCCTTGT | GGCTCTACAG | GACGGGAAGA | AAAGTGCAAG | AGACAGACAA | 3550 |
| GCACGGAACA | CCGAGATGTC | CTGCCCTTCT | TTTCACGTTC | TCTGTCTGTT | |
| AGACTACAGT | GTTCTTGCTG | GAAAGTCTGT | ATATATGTCT | GCGTATGTGA | 3600 |
| TCTGATGTCA | CAAGAACGAC | CTTTCAGACA | TATATACAGA | CGCATACACT | |
| GTGTGTGAAC | GCATGATTTT | ACTTTGGGGG | TGTATGATCA | GACATATATC | 3650 |
| CACACACTTG | CGTACTAAAA | TGAAACCCCC | ACATACTAGT | CTGTATATAG | |
| AGTTCCTCTT | GTCCAAGCAC | ACACTTTTGG | AAACTTTGTC | TTGTATTATT | 3700 |
| TCAAGGAGAA | CAGGTTCGTG | TGTGAAAACC | TTTGAAACAG | AACATAATAA | |
| TATGGTATTT | TGAGTGGGTG | CGGTACCTGT | ACTAATTAAC | TATTATTGAT | 3750 |
| ATACCATAAA | ACTCACCCAC | GCCATGGACA | TGATTAATTG | ATAATAACTA | |
| GGTCGTATTT | ATTGAACTAA | AATAAACTGA | AGACATTTTC | CCAGTC | 3796 |
| CCAGCATAAA | TAACTTGATT | TTATTTGACT | TCTGTAAAAG | GGTCAG | |

Fig._1F

```
Met Gln Cys Pro Pro Ile Leu Leu Val Trp Thr Leu Trp Ile Met Ala
1               5                   10                  15

Val Asp Cys Ser Arg Pro Lys Val Phe Leu Pro Ile Gln Pro Glu Gln
                20              25              30

Glu Pro Leu Gln Ser Lys Thr Pro Ala Gly Cys Thr Phe Gly Gly Lys
        35              40              45

Phe Tyr Ser Leu Glu Asp Ser Trp His Pro Asp Leu Gly Glu Pro Phe
    50              55              60

Gly Val Met His Cys Val Leu Cys Tyr Cys Glu Pro Gln Arg Ser Arg
65              70              75                  80

Arg Gly Lys Pro Ser Gly Lys Val Ser Cys Lys Asn Ile Lys His Asp
                85              90              95

Cys Pro Ser Pro Ser Cys Ala Asn Pro Ile Leu Leu Pro Leu His Cys
            100             105             110

Cys Lys Thr Cys Pro Lys Ala Pro Pro Pro Ile Lys Lys Ser Asp
        115             120             125

Phe Val Phe Asp Gly Phe Glu Tyr Phe Gln Glu Lys Asp Asp Asp Leu
        130             135             140

Tyr Asn Asp Arg Ser Tyr Leu Ser Ser Asp Val Ala Val Glu Glu
145             150             155             160

Ser Arg Ser Glu Tyr Val Ala Leu Leu Thr Ala Pro Ser His Val Trp
            165             170             175

Pro Pro Val Thr Ser Gly Val Ala Lys Ala Arg Phe Asn Leu Gln Arg
            180             185             190

Ser Asn Leu Leu Phe Ser Ile Thr Tyr Lys Trp Ile Asp Arg Leu Ser
        195             200             205

Arg Ile Arg Phe Ser Asp Leu Asp Gly Ser Val Leu Phe Glu His Pro
210             215             220
```

Fig._2A

| | | | | | | | | | | | | | | |
|---|---|---|---|---|---|---|---|---|---|---|---|---|---|---|
|Val|His|Arg|Met|Gly|Ser|Pro|Arg|Asp|Asp|Thr|Ile|Cys|Gly|Ile|Trp|
|225| | | | |230| | | |235| | | | |240|

Val His Arg Met Gly Ser Pro Arg Asp Asp Thr Ile Cys Gly Ile Trp
225           230              235              240

Arg Ser Leu Asn Arg Ser Thr Leu Arg Leu Arg Met Gly His Ile
            245              250              255

Leu Val Ser Leu Val Thr Thr Thr Leu Ser Glu Pro Glu Ile Ser Gly
            260              265              270

Lys Ile Val Lys His Lys Ala Leu Phe Ser Glu Ser Phe Ser Ala Leu
            275              280              285

Leu Thr Pro Glu Asp Ser Asp Glu Thr Gly Gly Gly Gly Leu Ala Met
290              295              300

Leu Thr Leu Ser Asp Val Asp Asp Asn Leu His Phe Ile Leu Met Leu
305              310              315              320

Arg Gly Leu Ser Gly Glu Glu Gly Asp Gln Ile Pro Ile Leu Val Gln
                325              330              335

Ile Ser His Gln Asn His Val Ile Arg Glu Leu Tyr Ala Asn Ile Ser
            340              345              350

Ala Gln Glu Gln Asp Phe Ala Glu Val Leu Pro Asp Leu Ser Ser Arg
            355              360              365

Glu Met Leu Trp Leu Ala Gln Gly Gln Leu Glu Ile Ser Val Gln Thr
    370              375              380

Glu Gly Arg Arg Pro Gln Ser Met Ser Gly Ile Ile Thr Val Arg Lys
385              390              395              400

Ser Cys Asp Thr Leu Gln Ser Val Leu Ser Gly Gly Asp Ala Leu Asn
            405              410              415

Pro Thr Lys Thr Gly Ala Val Gly Ser Ala Ser Ile Thr Leu His Glu
            420              425              430

Asn Gly Thr Leu Glu Tyr Gln Ile Gln Ile Ala Gly Thr Met Ser Thr
            435              440              445

Fig._2B

```
Val Thr Ala Val Thr Leu Glu Thr Lys Pro Arg Arg Lys Thr Lys Arg
        450             455             460

Asn Ile Leu His Asp Met Ser Lys Asp Tyr His Asp Gly Arg Val Trp
465             470             475             480

Gly Tyr Trp Ile Asp Ala Asn Ala Arg Asp Leu His Met Leu Leu Gln
                485             490             495

Ser Glu Leu Phe Leu Asn Val Ala Thr Lys Asp Phe Gln Glu Gly Glu
            500             505             510

Leu Arg Gly Gln Ile Thr Pro Leu Leu Tyr Ser Gly Leu Trp Ala Arg
        515             520             525

Tyr Glu Lys Leu Pro Val Pro Leu Ala Gly Gln Phe Val Ser Pro Pro
        530             535             540

Ile Arg Thr Gly Ser Ala Gly His Ala Trp Val Ser Leu Asp Glu His
545             550             555             560

Cys His Leu His Tyr Gln Ile Val Val Thr Gly Leu Gly Lys Ala Glu
                565             570             575

Asp Ala Ala Leu Asn Ala His Leu His Gly Phe Ala Glu Leu Gly Glu
            580             585             590

Val Gly Glu Ser Ser Pro Gly His Lys Arg Leu Leu Lys Gly Phe Tyr
        595             600             605

Gly Ser Glu Ala Gln Gly Ser Val Lys Asp Leu Asp Leu Glu Leu Leu
        610             615             620

Gly His Leu Ser Arg Gly Thr Ala Phe Ile Gln Val Ser Thr Lys Leu
625             630             635             640

Asn Pro Arg Gly Glu Ile Arg Gly Gln Ile His Ile Pro Asn Ser Cys
                645             650             655

Glu Ser Gly Gly Val Ser Leu Thr Pro Glu Glu Pro Glu Tyr Glu Tyr
            660             665             670
```

Fig. 2C

Glu Ile Tyr Glu Glu Gly Arg Gln Arg Asp Pro Asp Leu Arg Lys
        675                 680             685

Asp Pro Arg Ala Cys Ser Phe Glu Gly Gln Leu Arg Ala His Gly Ser
    690             695                 700

Arg Trp Ala Pro Asp Tyr Asp Arg Lys Cys Ser Val Cys Ser Cys Gln
705             710                 715                 720

Lys Arg Thr Val Ile Cys Asp Pro Ile Val Cys Pro Pro Leu Asn Cys
            725                 730                 735

Ser Gln Pro Val His Leu Pro Asp Gln Cys Cys Pro Val Cys Glu Glu
            740                 745                 750

Lys Lys Glu Met Arg Glu Val Lys Lys Pro Glu Arg Ala Arg Thr Ser
            755                 760                 765

Glu Gly Cys Phe Phe Asp Gly Asp Arg Ser Trp Lys Ala Ala Gly Thr
    770                 775                 780

Arg Trp His Pro Phe Val Pro Pro Phe Gly Leu Ile Lys Cys Ala Ile
785                 790                 795                 800

Cys Thr Cys Lys Gly Ser Thr Gly Glu Val His Cys Glu Lys Val Thr
                805                 810                 815

Cys Pro Lys Leu Ser Cys Thr Asn Pro Ile Arg Ala Asn Pro Ser Asp
            820                 825                 830

Cys Cys Lys Gln Cys Pro Val Glu Glu Arg Ser Pro Met Glu Leu Ala
            835                 840                 845

Asp Ser Met Gln Ser Asp Gly Ala Gly Ser Cys Arg Phe Gly Arg His
    850                 855                 860

Trp Tyr Pro Asn His Glu Arg Trp His Pro Thr Val Pro Pro Phe Gly
865                 870                 875                 880

Glu Met Lys Cys Val Thr Cys Thr Cys Ala Glu Gly Ile Thr Gln Cys
                885                 890                 895

Fig._2D

Arg Arg Gln Glu Cys Thr Gly Thr Thr Cys Gly Thr Gly Ser Lys Arg
        900                 905             910

Asp Arg Cys Cys Thr Lys Cys Lys Asp Ala Asn Gln Asp Glu Asp Glu
        915             920             925

Lys Val Lys Ser Asp Glu Thr Arg Thr Pro Trp Ser Phe
930             935             940

Fig._2E

| | | | | | |
|---|---|---|---|---|---|
| GGCCAACACC | TCCGcTCAGG | AGCCAGGTtT | TGCTGAGGTG | CTGCCCAGCC | 50 |
| TTACAGACCA | AGAGATGGAC | TGGTTGGAGC | TGGGGGAGCT | GCAGATGGTC | 100 |
| CTAGAGAAGG | CGGGTGGgcC | AGAGCTACGC | ATCAGTGGAT | ACATCACCAC | 150 |
| CAGGNAGAGC | TGTGATGTCC | ttCAAAGTGT | CCTNTGTGGt | GgTGATGCCC | 200 |
| TGATCCCAGt | CCAGACGGGT | GCTGCTGGaT | CAGACAGCTT | CATATTGNTA | 250 |
| GGAAATGGCT | CCCTTATCTA | TCAGGTACAA | GTGGTAGGTA | CAGGTAGCGA | 300 |
| GGTGGTGGcC | ATAACACTGG | AGACCAaCCC | TCAGgGGAAG | | 340 |

Fig._3

DNA ENCODING A TISSUE DIFFERENTIATION AFFECTING FACTOR

This invention was made with Government support under grant contract number HD-21502, awarded by the National Institutes of Health. The Government has certain rights in this invention.

FIELD OF THE INVENTION

The invention generally relates to growth factors, neurotrophic factors, and their inhibitors, and more particularly to a growth factor with dorsal growth (and neural tissue) inducing activity, to complexes and compositions including the factor, and to DNA or RNA coding sequences for the factor, and to factors of the same family.

BACKGROUND OF THE INVENTION

Growth factors are substances, such as polypeptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines, trophic factors, and their inhibitors. Among growth, or neurotrophic, factors presently known are the transforming growth factors (TGF-α, TGF-β, TGF-γ)]. Transforming growth factor-β appears to elicit a variety of responses in many different cell types.

Widespread neuronal cell death accompanies normal development of the central and peripheral nervous systems. Studies of peripheral target tissues during development have shown that neuronal cell death results from the competition among neurons for limiting amounts of survivor factors ("neurotrophic factors"). The earliest identified of these, nerve growth factor ("NGF"), is the most fully characterized and has been shown to be essential for the survival of sympathetic and neural crest-derived sensory neurons during early development of both chick and rat. Barde et al., U.S. Pat. No. 5,229,500, issued Jul. 20, 1993, describe nucleic acid sequences encoding brain derived neurotrophic factor ("BDNF"), as well as the BDNF protein. BDNF is suggested for treating Parkinson's Disease and Alzheimer's Disease. Additional uses (quite recently performed successfully) are for the identification of homologous regions between BDNF and NGF so as to identify and isolate additional members of the NGF family, and also to generate immunogen by antibodies directed toward BDNF or fragments.

Among TGF-β members are the bone morphogenetic proteins (BMP). The BMPs have been indicated as useful in wound healing, tissue repair, and to induce cartilage and/or bone growth. For example, PCT Application 9309229, inventors Israel and Wolfman, published May 13, 1993, describes uses of proteins with bone stimulating activity such as bone fracture healing and possibly the treatment of periodontal disease and other tooth repair processes.

BMPs have potent effects during embryogenesis. One member, BMP-4, has been shown to have potent ventralizing effects in Xenopus embryos, leading to the differentiation of blood and mesenchyme and inhibiting the formation of dorsal tissues such as notochord, muscle, and nervous system. (See, e.g., Jones et al., *Development*, 115, pp. 639–647, 1991.) BMP-4 is expressed ventrally in the Xenopus embryo and its expression is increased by ventralizing treatments such as irradiation with ultraviolet light (UV), see Steinbeisser et al., *EMBO J.*, in press, November 1994 issue.

An inhibitor of ventralizing BMPs could have dorsalizing effects on tissue differentiation. There are precedents for such inhibitory interactions in the TGF-β family, since activin, a dorsalizing factor, can be inhibited by a specific inhibitory protein designated inhibin in the Xenopus embryo. (See, e.g., Hemmati-Brivanlou et al., *Cell*, 77, pp. 283–295, 1994.)

Another family of neurotropic factors are the Wnts, which have dorsal axis-inducing activity. Most of the Wnt protein are bound to cell surfaces. (See, e.g., Sokol et al., *Science*, 249, pp. 561–564, 1990.) One member of the family, Xwnt-8, was described as to dorsal axis-inducing activity in Xenopus embryos by Smith and Harland in 1991, *Cell*, 67, pp. 753–765. The authors described using RNA injections as a strategy for identifying endogenous RNAs involved in dorsal patterning to rescue dorsal development in embryos that were ventralized by UV irradiation.

Uv ventralization is useful to probe the normal response of a gene to dorsal/ventral cell identity because UV treated embryos reproducibly lack obvious dorsal structures (e.g. somites, notochord, and neural plate). In addition, gastrulae that has become extreme ventralized tadpoles form a radial blastopore lip at the time of normal ventral blastopore lip formation. This suggests that the mesoderm is behaving as though it is ventral in identity. Lithium chloride treatment respecifies the fate of cells along the anterior-posterior axis of the early embryo by contrast to UV irradiation, which causes centralization of embryos.

Another member of the Wnt family was subsequently discovered and described by Harland and Smith, which they termed "noggin." (*Cell*, 70, pp. 829–840 (1992).)

Noggin is a good candidate to function as a signaling molecule in Nieuwkoop's center, by virtue of its maternal transcripts, and in Spemann's organizer, through its zygotic organizer-specific expression. Besides noggin, other secreted factors many be involved in the organizer phenomenon.

New growth and neurotrophic factors are being sought, particularly those that are secreted due to their ability to be used in physiologically active, soluble forms because these factors, their receptors, and DNA or RNA coding sequences therefore and fragments thereof are useful in a number of therapeutic, clinical, research, diagnostic, and drug design applications.

SUMMARY OF THE INVENTION

In one aspect of the present invention, a peptide that can be in substantially purified form is encoded by SEQ ID NO:1. The Xenopus SEQ ID NO:1 codes for a functional polypeptide that we have designated "chordin," which is capable of inducing dorsal (and neural tissue) development in vertebrates when expressed, and whose deduced amino acid sequence is illustrated by SEQ ID NO:2. Since peptides of the invention induce dorsal and neural tissue differentiation in vertebrates, they should be able to be prepared in physiologically active form for a number of therapeutic, clinical, and diagnostic applications.

In another aspect of the present invention an oligonucleotide, such as cDNA, is provided having the complementary sequence to SEQ ID NO:1. This oligonucleotide can be single or double stranded, be formed of DNA or RNA bases, and can be in the antisense direction, as illustrated by SEQ ID NO:1.

Chordin or fragments thereof (which also may be synthesized by in vitro methods) may be fused (by recombinant expression or in vitro covalent methods) to an immunogenic polypeptide and this, in turn, may be used to immunize an animal in order to raise antibodies against a chordin epitope. Anti-chordin is recoverable from the serum of immunized animals. Alternatively, monoclonal antibodies may be prepared from cells to the immunized animal in conventional fashion. Immobilized anti-chordin antibodies are useful particularly in the diagnosis (in vitro or in vivo) or purification of chordin.

Substitutional, deletional, or insertional mutants of chordin and polypeptides derived from its sequence may be prepared by in vitro or recombinant methods and screened for immuno-crossreactivity with chordin and for chordin antagonist or agonist activity.

Chordin also may be derivatized in vitro in order to prepare immobilized chordin and labelled chordin, particularly for purposes of diagnosis of insufficiencies of chordin or its antibodies, or for affinity purification of chordin antibodies.

BRIEF DESCRIPTION OF THE DRAWINGS

FIGS. 1A, 1B, 1C, 1D, 1E and 1F illustrates a cDNA clone (SEQ ID NO:1) for chordin derived from Xenopus. Sense strand is on top (5' to 3' direction) and the antisense strand on the bottom line (in the opposite direction);

FIGS. 2A, 2B, 2C, 2D, and 2E illustrates the predicted translated amino acid sequence (SEQ ID NO:2) of the FIGS. 1A, 1B, 1C, 1D, 1E and 1F cDNA clone for chordin; and FIG. 3 illustrates the preliminary nucleotide sequence (sense strand) of a partial mouse chordin cDNA clone (SEQ ID NO:3). Nucleotides indicted by lower case letters are prone to errors, and N indicates that it was not possible to identify any particular nucleotides at this position in this preliminary automated nucleotide sequence determination.

DESCRIPTION OF THE PREFERRED EMBODIMENTS

We have discovered a novel dorsalizing and neural inducing factor that induces dorsal development in vertebrates that we have named "chordin." When referring to chordin, the present invention also contemplates the use of fragments, derivatives, agonists, or antagonists of chordin molecules.

Chordin is expressed in the Spemann organizer. In UV-treated embryos, a single injection of synthetic chordin mRNA can completely rescue axial development. This rescue is dose-dependent and sensitive to 2-fold differences in the amount of injected mRNA. In the UV rescue assay, the effect of chordin is similar to that of Xwnt-8 mRNA (Sokol et al., supra, 1990; Smith and Harland, supra, 1991) and noggin (Smith and Harland, supra, 1992). However, although the phenotypes are similar, Xwnt-8 is expressed in the ventral and lateral marginal zone but not in the organizer region, and therefore is unlikely to act as a dorsalizing signal in vivo. Chordin expression overlaps, in part, with that of noggin.

Thus, noggin and chordin are both dorsalizing factors with some similar phenotypic effects. Since noggin is expressed maternally and zygotically, the latter expression being localized in the organizer, noggin could function in the Nieuwkoop center, the Spemann organizer, or both. On the other hand, chordin is expressed only zygotically and exclusively in the organizer region, so that it could not function in vivo in the Nieuwkoop center. There are no sequence similarities between the two proteins; noggin encodes a secreted polypeptide of 222 amino acids while chordin is four times as large.

Chordin and noggin display clear cut differences in their modes of activation. Noggin is a primary response gene to activin induction, while chordin is a secondary response gene requiring de novo protein synthesis. In addition, chordin is activated by the organizer-specific homeobox genes gsc and Xnot2, while noggin is not. Thus, despite some phenotypic similarities in embryological assays, chordin and noggin appear to represent two parallel signalling pathways in Spemann's organizer.

To illustrate the mechanism underlying the biological activity of chordin, we studied mesoderm induction in animal cap explants. Injection of chordin mRNA did not induce mesoderm by itself, but promoted induction of notochord and neural tissues in animal caps treated with bFGF. Similar observations, in which dorsalizing agents cannot induce mesoderm in animal caps but can form dorsal mesoderm, in response to ventral mesoderm induction, have been reported, for example, with noggin and Xwnt-8 mRNA. Since the expression of chordin is zygotic and localized specifically in the organizer, this molecule, like noggin, appears to be a horizontal dorsalizing signal.

The amphibian organizer consists of several cell populations with region-specific inducing activities. On the basis of morphogenetic movements, three very different cell populations can be distinguished in the organizer. First, cells with crawling migration movements involute, fanning out to form the prechordal plate. Second, cells involute through the dorsal lip driven by convergence and extension movements, giving rise to the notochord of the trunk. Third, involution ceases and the continuation of mediolateral intercalation movements leads to posterior extension movements and to the formation of the tail notochord and of the chordoneural hinge. The three cell populations correspond to the head, trunk, and tail organizers, respectively.

Despite their different behaviors from the cell biological point of view, the three organizer regions share a common dorsalizing and neural inducing molecule, we call chordin, which is expressed at the right time and in the right place to participate in cell signalling by Spemann's organizer and is activated by organizer-specific homeobox genes.

Our studies were conducted in early embryos of the frog Xenopus laevis. The frog embryo is well suited to experiments, particularly experiments pertaining to generating and maintaining regional differences within the embryo for determining roles in tissue differentiation. It is easy to culture embryos with access to the embryos even at very early stages of development (preceding and during the formation of body pattern and differentiation) and the embryos are large. The initial work with noggin also had been in Xenopus embryos, and, as predicted, was highly conserved among vertebrates so that the predictions based on work with Xenopus as to corresponding human noggin were proven true and the ability to clone the gene for human noggin was readily accomplished. (See the description of Xenopus work and cloning information in PCT application, published Mar. 17, 1994, WO 9 405 800, and the subsequent human cloning based thereon in the PCT application, also published Mar. 17, 1994, as WO 9 405 791.)

Chordin therefore is believed to be a secreted protein, has 941 amino acids, and is expressed specifically in the head-, trunk-, and tail-organizer regions of the Xenopus embryo. The human counterpart is expected to have properties predicted from our recent isolation of a mammalian cDNA with similarity to Xenopus chordin. This cDNA was isolated from a gastrula cDNA library made in this laboratory from 6½ to 7½ day mouse embryos, by screening with the Xenopus probe under conditions of moderate stringency. Mouse chordin is expressed in the embryo in a region homologous to Spemann's organizer, the murine node. In the genome, this cDNA maps to mouse chromosome 16, within one centimorgan of marker D16MIT1. Because this region of the mouse genome is considered homologous, or synthenic, to specific regions of either human chromosomes 22 or 3, see Lyons and Searle, eds., *Genetic Variants and Strains of the Laboratory Mouse*, second ed., Oxford University Press (1989), p. 531, one can predict the genomic location of the human gene. While the sequence of the mouse cDNA is not complete at this time there are substantial regions of conservation with Xenopus chordin (FIG. 3, SEQ ID NO:3). For example, the mouse cDNA has predicted polypeptides of amino acid sequence SAQEPGFAEVLP, SCDVLQSVLCGGDAL, and AITLETNP, which have only two amino acid differences each with the Xenopus chordin sequence shown in FIG. 2A–E (SEQ ID NO:2). Such regions of high identity between Xenopus and mouse chordin predict that the human gene will also be similar in these regions. Further, it predicts that it should be very feasible to use these regions of high homology to isolate the human chordin gene by high or medium stringency hybridization, or by the polymerase chain reaction. Such conserved regions may also help to isolate not only the human homolog of chordin, but also other family members of the chordin family. Secreted signalling factors, such as the Wnts and BMPs discussed above, are frequently part of families of related proteins, which may have similar or divergent functions.

We have cloned a full length Xenopus cDNA for chordin. The chordin cDNA contains a reading frame encoding a 941 residue, 105 kDa precursor protein with a hydrophobic amino-terminal sequence. The sequence predicts a mature, carboxy-terminal, processed product of 103 kDa.

Chordin has the ability to modify mesoderm induction of embryonic cells, so that neural, muscle, and other tissues are induced. Thus, this entirely new molecule has demonstrated physiological properties that should prove useful in therapeutic, diagnostic, and clinical applications that require regeneration, differentiation, or repair of tissues, such wound repair, neuronal regenerational or transplantation, supplementation of muscle differentiation, bone tissue repair, and other applications in which embryonic cellular processes are to be induced.

Chordin nucleic acids, or oligonucleotides, encode a chordin polypeptide or hybridize to such DNA and remain stably bound to it under stringent conditions and are greater than about 10 bases in length. By "stringent conditions" we mean those which (1) employ low ionic strength and high temperature for washing, for example, 0.15M NaCl/0.015M sodium citrate/0.1% NaDodSo₄ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

By "substantial similarity," when we are referring to a nucleotide sequence, is meant cross hybridization of sequences under conditions of moderate stringency using a probe greater than about 100 nucleotides long at 30° C. in a standard buffer (Wahl et al., PNAS, 76, 3683) and washes at 37° C. in 300 mM NaCl, 30 mM sodium citrate, 0.2% SDS at pH 7. Alternatively, one is able to isolate, by polymerase chain reaction, a fragment of DNA coding for chordin or chordin family members when using primers of degenerate sequence.

By "substantial similarity" when reference is made to proteins is that chordin from different species, or chordin family members within a species, have stretches of 10 consecutive amino acids or more having 80% identity in amino acid sequence.

Similarity at the protein level includes an ability of a subject protein to compete with chordin for binding to receptors or other interacting proteins and some (but not all) monoclonal antibodies raised against chordin epitopes.

The cloned cDNA for chordin (derived from frog) is designated herein as SEQ ID NO:1. We have used RNA transcripts from the SEQ ID NO:1 clone to rescue embryos and return them to substantially normal development when the chordin RNA is injected into ventralized embryos.

A number of applications for chordin are suggested from its pharmacological (biological activity) properties.

The chordin cDNA should be useful as a diagnostic tool (such as through use of antibodies in assays for proteins in cell lines or use of oligonucleotides as primers in a PCR test to amplify those with sequence similarities to the oligonucleotide primer, and to see how much chordin is present).

Without being bound by theory, we have formulated hypotheses about the embryological effects of chordin based on where it is expressed, and on the effects of RNA injection in embryos. Since chordin is expressed in the Spemann organizer, we believe chordin to be a mediator of the effects of the Spemann organizer, namely neural induction and dorsalization of the mesoderm. Since chordin is expressed in the notochord and head mesoderm, we believe chordin to influence either the dorsal-ventral pattern or anterior-posterior pattern of the neural plate. Since chordin is expressed in the branchial arch neural crest, we believe it may therefore influence whether neural crest cells deposit cartilage and also to influence later branchial arch growth and remodelling. Chordin is expressed in the tail fin neural crest, and since neural crest is required for growth of the fin, chordin may act as a growth factor for epidermis or mesenchyme.

Since chordin is able to modify the action of FGF so that differentiation of many tissues is induced, such as somite and its derivatives (muscle, cartilage, and at later stages bone) and neural tissue and its derivatives (neural crest and sensory placodes), we believe that chordin may influence the differentiation and growth of many tissues. Clinical uses to regulate cartilage and bone regeneration, wound healing, and neural regeneration and transplantation are suggested. In these processes, cells adopt the properties of embryonic cells, and chordin may be especially useful in therapeutic compositions including other growth factors active in embryogenesis.

One hypothesis that is particularly attractive is that chordin, which is expressed dorsally, may antagonize the activity of BMP-4, or other growth factors, that are expressed ventrally. BMP-4 has such potent ventralizing activity, see Fainsod et al., supra, (1994), that interfering with its activity may result in dorsal development. Further support for this hypothesis comes from the recent observation that dominant-negative receptors that interfere with signalling of multiple BMPs in the Xenopus embryo lead to some dorsal development (muscle) in ventralized embryos. (See, Graft et al., *Cell*, 79, pp. 169–179, 1994.) If such a negative action of chordin on signalling by BMPs of other growth factors existed, it could act at many different levels, by binding directly to BMPs, or by modifying the proteolytic processing or transport of BMPs in the extracellular matrix, or by interfering with BMP receptors. These might be properties of the entire chordin molecule or of shorter peptides derived from it by proteolysis.

Chordin, of course, might act upon its target cells via its own receptor. Chordin, therefore, provides the key to isolate this receptor. Since many receptors mutate to cellular oncogenes, the chordin receptor should prove useful as a diagnostic probe for certain tumor types. Thus, when one views chordin as ligand in complexes, then complexes in accordance with the invention include antibody bound to chordin, antibody bound to peptides derived from chordin, chordin bound to its receptor, or peptides derived from chordin bound to its receptor or other factors. Mutant forms of chordin, which are either more potent agonists or antagonists, are believed to be clinically useful. Such complexes of chordin and its binding protein partners will find uses in a number of applications.

Practice of this invention includes use of an oligonucleotide construct comprising a sequence coding for chordin and for a promoter sequence operatively linked to chordin in a mammalian or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. The well-known plasmid pBR322 is suitable for most gram negative bacteria, the 2μ plasmid origin for yeast and various viral origins (SV40, polyoma, adenovirus, VSV or BPV) are useful for cloning vectors in mammalian cells.

Expression and cloning vectors should contain a selection gene, also termed a selectable marker. Typically, this is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies.

Examples of suitable selectable markers for mammalian cells are dihydrofolate reductase (DHFR) or thymidine kinase. Such markers enable the identification of cells which were competent to take up the chordin nuclei acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed. Amplification is the process by which genes in greater demand for the production of a protein critical for growth are reiterated in tandem within the chromosomes of successive generations of recombinant cells. Increased quantities of chordin can therefor be synthesized from the amplified DNA.

For example, cells transformed with the DHFR selection gene are first identified by culturing all of the transformants in a culture medium which contains methotrexate (Mtx), a competitive antagonist of DHFR. An appropriate host cell in this case is the Chinese hamster ovary (CHO) cell line deficient in DHFR activity, prepared and propagated as described by Urlaub and Chasin, *Proc. Nat. Acac. Sci.*, 77, 4216 (1980). The transformed cells then are exposed to increased levels of Mtx. This leads to the synthesis of multiple copies of the DHFR gene and, concomitantly, multiple copies of other DNA comprising the expression vectors, such as the DNA encoding chordin. Alternatively, host cells transformed by an expression vector comprising DNA sequences encoding chordin and aminoglycoside 3' phosphotransferase (APH) protein can be selected by cell growth in medium containing an aminoglycosidic antibiotic such as kanamycin or neomycin or G418. Because eukarotic cells do not normally express an endogenous APH activity, genes encoding APH protein, commonly referred to as neo resistant genes, may be used as dominant selectable markers in a wide range of eukaryotic host cells, by which cells transformed by the vector can readily be identified.

Expression vectors, unlike cloning vectors, should contain a promoter which is recognized by the host organism and is operably linked to the chordin nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters can be operably linked to chordin encoding DNA by removing them from their gene of origin by restriction enzyme digestion, followed by insertion 5' to the start codon for chordin.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exit then synthetic oligonucleotide adapters or linkers are used in accord with conventional practice.

Transcription of chordin-encoding DNA in mammalian host cells is controlled by promoters obtained from the genomes of viruses such as polyoma, cytomegalovirus, adenovirus, retroviruses, hepatitis-B virus, and most preferably Simian Virus 40 (SV40), or from heterologous mammalian promoters, e.g. the actin promoter. Of course, promoters from the host cell or related species also are useful herein.

Chordin is clearly useful as a component of culture media for use in culturing cells, such as nerve cells, in vitro. We believe chordin will find use as an agent for enhancing the survival or inducing the growth of nerve and muscle cells. It may, therefore, be found useful in the therapy of degenerative disorders of the nervous system ("neurodegenerative diseases"), including such diseases as Alzheimer's disease, Parkinson's disease, Huntington's chorea, ALS, peripheral neuropathies, and other conditions characterized by necrosis or loss of neurons, whether central, peripheral, or motor-neurons. In addition, it may be useful for treating damaged nerve cells, e.g., nerves damaged by traumatic conditions such as burns and wounds, diabetes, kidney dysfunction, and the toxic effects of chemotherapeutics used to treat cancer and AIDS.

Practice of this invention includes preparation and uses of a diagnostic or therapeutic agent comprising a nucleotide sequence preferably having at least about 15 DNA or RNA bases analogous to all or a portion of either SEQ ID NO:1 or SEQ ID NO:3. That is, chordin preparations are useful as standards in assays for chordin and in competitive-type receptor binding assays when labelled with radioiodine, enzymes, fluorophores, spin labels, and the like. Therapeutic formulations of chordin are prepared for storage by mixing chordin having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; anti-oxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Polyclonal antibodies to chordin generally are raised in animals by multiple subcutaneous (sc) or intraperitoneal (ip) injections of chordin and an adjuvant. It may be useful to conjugate chordin or a fragment containing the target amino acid sequence to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$.

Animals can be immunized against the immunogenic conjugates or derivatives by combining 1 mg or 1 µg of conjugate (for rabbits or mice, respectively) with 3 volumes of Freund's complete adjuvant and injecting the solution intradermally in multiple sites. One month later the animals are boosted with ⅕ to ¹/₁₀ the original amount of conjugate in Fruend's complete adjuvant by subcutaneous injection at multiple sites. Seven to 14 days later animals are bled and the serum is assayed for anti-chordin titer. Animals are boosted until the titer plateaus. Preferably, the animal is boosted with the conjugate of the same chordin polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

Chordin antibodies are useful in diagnostic assays for chordin or its antibodies and to identify family members. In one embodiment of a receptor binding assay, an antibody composition which binds to all of a selected plurality of members of the chordin family is immobilized on an insoluble matrix, the test sample is contacted with the immobilized antibody composition in order to adsorb all chordin family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

Chordin antibodies also are useful for the affinity purification of chordin from recombinant cell culture or natural sources. Chordin antibodies that do not detectably cross-react with other growth factors can be used to purify chordin free from these other family members.

Chordin encodes a putative secreted protein of 941 amino acids. It has four cys-rich domains similar to those found in extracellular proteins such as thrombospondin, the propeptide of alpha procollagen, and von Willebrand factor. The conservation is limited mostly to the spacing of the cysteine residues; it appears that the cys-rich domains define a novel family of secreted, extracellular matrix or cell surface proteins. Chordin, like other proteins containing cys-rich repeats, may be a matrix protein. A role for extracellular matrix proteins in patterning signals would not be unprecedented; recently one of the signals involved in axon guidance by the floor plate has been identified as netrin, a protein with homology to laminin B2.

Most of the chordin protein sequence shows no significant homology to known proteins. Although the function of cys-rich domains is unknown, they have been implicated in protein multimerization. In the case of alpha-1 procollagen types I and III, a propeptide including the cys-rich domain has been proposed to be involved in negative feedback of collagen expression. Thus, the cys-rich repeats could contain part of the biological activity of chordin, and may be released by proteolytic cleavage.

EXPERIMENTAL RESULTS

To isolate dorsal-specific genes, duplicate filters of an unamplified dorsal lip cDNA library (Blumberg et al, *Science*, 253, pp. 194–196, 1991) were hybridized with probes synthesized either from dorsalized or ventralized gastrula mRNAs. To enrich for zygotically expressed genes, the probes were subtracted with maternal (8-cell embryo) mRNA. It is empirically known that many primary response genes to mesoderm induction in Xenopus are also expressed in egg mRNA, so this subtraction step should reduce the chance of recloning known genes such as gsc, Xlim, XFKH1 and Xnot, and increase the possibility of isolating downstream target genes. Screening of 25,000 plaques (see Experimental Procedures) yielded six independent groups of cDNAs enriched in LiCl-treated embryos.

To identify cDNAs of interest, further screening was performed with the longest clone of each group in three ways. 1) The ability of its sense RNA to induce secondary axes was explored by microinjection into ventral blastomeres. 2) Whole-mount in situ hybridization (Harland, 1991) using a mixture of embryos of different stages was used to identify clones expressed in areas of known organizing activity. 3) The activation of candidate genes by organizer-specific homeobox products was tested by whole-mount in situ hybridization of embryos microinjected with gsc mRNA at concentrations known to induce formation of secondary axes. In situ hybridization identified only one group, consisting of three clones which eventually proved not to be full-length, that was exclusively expressed in cells with Spemann's organizer activity. The gene encoding these cDNAs, chordin, was found to be activated by gsc and chosen for further study.

By in situ hybridization chordin transcripts are first detected one hour before gastrulation (stage 9½) in nuclei scattered in the dorsal marginal zone. When the dorsal lip is first detected at stage 10¼, the chordin transcript is found exclusively on the forming lip and cytoplasmic staining can also be observed. Once the dorsal lip is fully formed (stage 10¾), chordin expression is intense both in superficial and involuted cells. By the mid gastrula stage, when a circular blastopore is formed (stage 11), most cells expressing chordin have involuted (explaining the more diffuse appearance of the chordin signal), except for cells in the dorsal half of the edge of the lip itself.

At early neurula (stage 13), strong chordin expression is detected in the prechordal plate (head mesoderm) and the notochord. At the early tailbud stage (stage 26), chordin is transiently expressed in the forebrain, fading from the prechordal plate and anterior notochord but remaining in the posterior notochord and tailbud hinge. Later on (stage 33, corresponding to 42 hours of development), the chordin signal is detected exclusively in the tailbud. Closer examination reveals that the expression is localized in a specific region in the tailbud, the chordoneural hinge. This is of interest because transplantation experiments have shown that the chordoneural hinge retains organizer activity at this stage. Expression continues in the tip of the tail in swimming tadpoles (stage 42, 72 hours after fertilization). In embryos dorsalized by LiCl treatment chordin expression is enhanced, forming a ring that spans the entire marginal zone; this explains why the gene was isolated in the differential screen. All observations mentioned above were confirmed in embryos rendered transparent by clearing solution and in histological sections.

Taken together, these descriptive studies show that chordin is expressed initially in the dorsal lip and then in tissues derived from the organizer. The expression in the dorsal lip and prechordal plate overlaps in part with that of the homeobox gene gsc. The later expression of chordin in the notochord and chordoneural hinge does not coincide with that of gsc but does overlap with the expression of another homeobox gene, Xnot2. These data led to the hypothesis that the chordin gene might be positively regulated (directly or indirectly) by both homeodomain proteins.

To test this hypothesis, synthetic gsc or Xnot2 mRNAs were microinjected radially into all blastomeres of 4-cell embryos, and hybridized with a chordin probe at the gastrula stage. Both gsc mRNA and Xnot2 mRNA were able to induce ectopic patches of chordin mRNA in the ventral and lateral marginal zone. We also tested whether chordin could be activated in embryos lacking an organizer. In UV-treated embryos, chordin expression is eliminated in keeping with the dorsal character of this gene. When UV-treated embryos were injected diagonally into two blastomeres at the 4-cell stage, two patches of chordin expression could be induced both by gsc and Xnot2 mRNAs.

The activation by these homeobox genes appears to be specific for chordin. Radial injection of gsc or Xnot2 mRNA did not cause ectopic expression of the organizer-specific gene noggin. In addition to providing a convenient negative control, the inability of gsc to activate noggin in this assay suggests that noggin is unlikely to mediate the non-cell-autonomous effects of gsc. As a further control, a biologically active homeobox mRNA of the Antennapedia-type (XlHbox 1); was injected and found not to activate chordin expression (even at 5-fold higher concentrations than those used for gsc and Xnot2 mRNA). An unrelated control synthetic mRNA (human prolactin) also failed to activate chordin.

We conclude that expression of chordin, but not that of noggin, can be activated by the gsc and Xnot2 homeobox gene products. The expression patterns of these transcription factors partially overlap with that of chordin; the effects of Xlim-1 and XFKH1, which also overlap in expression with chordin, were not tested in this study.

Activin is a potent inducer of dorsal mesoderm. Several genes can be activated by this growth factor even in the absence of de novo protein synthesis. Such Xenopus primary response genes include Mix-1, Brachyury, gsc, Xlim-1, XFKH1, and Xnot. Since gsc and Xnot2 can induce ectopic expression of chordin mRNA, it was of interest to test whether chordin is also a primary response gene to mesoderm induction or whether it is activated subsequent to the expression of organizer-specific homeobox genes.

Northern blot analysis was used to compare the temporal expression patterns of gsc and chordin. As noted previously, gsc has a maternal component and zygotic transcripts become detectable at stage 9, two hours before gastrulation starts. In contrast, chordin expression is not detectable until stage 9½, one hour before gastrulation starts. Thus, while gsc transcripts accumulate shortly after zygotic transcription starts at mid-blastula, those of chordin accumulate one hour later.

To test whether chordin is a primary or a secondary response gene, animal cap explants were incubated with activin in the presence or absence of cycloheximide (CHX), which inhibited protein synthesis by 95% (see Experimental Procedures). Chordin was induced by activin, but this induction was significantly decreased by CHX. In contrast, gsc induction by activin was somewhat increased by CHX, in agreement with previous observations. As noggin is an organizer-specific secreted factor, it was important, in the wider context of this study, to determine whether noggin is a primary response gene. Results indicate that noggin, like gsc, is a primary response gene because noggin transcripts were induced by activin in the presence of CHX (even to a higher level than in its absence).

Together with the time course, the animal cap studies indicate that the induction of chordin by activin treatment involves intermediate steps requiring de novo protein synthesis. Thus, the induction mechanism of chordin differs from that of other organizer-specific genes described to date, including noggin.

The three chordin cDNAs isolated in the initial screen were partial clones resulting from reverse transcriptase priming within an A-rich stretch within the coding sequence. These clones failed to reveal any biological activity in extensive microinjection experiments performed before sequence information was available. We re-screened the cDNA library and a full-length 3.8 kb chordin cDNA was isolated and sequenced (FIGS. 1A, 1B, 1C, 1D, 1E, and 1F SEQ ID NO:1). The deduced protein sequence of the longest open reading frame, chordin, encodes a large protein (predicted molecular weight of 105 kDa) of 941 amino acids (FIG. 2A–E). Hydropathy analysis showed a single hydrophobic segment comprising the 19 N-terminal amino acids, followed by a putative signal sequence cleavage site. The presence of a signal peptide and the lack of possible transmembrane segments suggest that chordin is a secreted protein. There are four possible N-glycosylation (NXS/T) sites. When compared to its own sequence by dot matrix alignment, the chordin protein was found to contain four internal repeats of 58 to 74 residues. Each repeat contains 10 cysteine residues at conserved positions as well as four other conserved amino acids.

When the cys-rich repeats were used to search the BLAST network databases, it was found that similar cys-rich repeats are present in several extracellular proteins. The conservation is restricted primarily to the spacing of Cys residues. Thrombospondin-1 and -2 and alpha-1 procollagen types I and III are extracellular matrix proteins that contain a single cys-rich domain near the amino terminus. Interestingly, these proteins are trimeric and the cys-rich domains may be involved in their multimerization. von Willebrand factor, a protein that facilitates adhesion of platelets during blood clotting, contains two cys-rich domains at its carboxy terminus (Hunt and Barker, BBRC, 144, pp. 876–882, 1987). More divergent cys-rich repeats of this type are found in extracellular proteins encoded by a growth factor-regulated gene (Simmons et al., PNAS USA, 86, pp. 1178–1182, 1989) and a Drosophila developmental gene (Schonbaum et al., Dev. Biol., 151, pp. 431–445, 1992).

Further, a just published report of the sequence of the Drosophila gene short gastrulation describes a protein of 1038 amino acids that, like chordin, has one cys-rich repeat at the amino terminus and three at the carboxy-terminus. (Francois et al., Genes and Development 8, pp. 2602–2616, Nov. 1, 1994.) While the overall structure is somewhat like that of chordin, the longest stretches of amino acid identity with chordin are one of six consecutive amino acids and another of five amino acids, both within the first cys-rich domain. Using the BESTFIT program, the two protein sequences are only 28.7% identical over the entire Sequences. Interestingly, short gastrulation is a putative negative growth factor that antagonizes the activity of decapentaplegic (dpp). (Ferguson and Anderson, Development, 114, pp. 583–597, 1992.) Dpp is a Drosophila protein of the BMP family. Thus, this finding reinforces the view that chordin may function as an antagonist of BMP function. While short gastrulation might be a fruit fly homolog of chordin, the sequence homology is too law to make this assumption without functional studies. Short gastrulation has the predicted structure of a type II transmembrane protein, which would have an intracellular stretch of 55 amino acids followed by a hydrophobic transmembrane domain. Chordin has a hydrophobic signal sequence at the amino terminus and thus has the characteristics of a typical secreted protein. In addition, the cys-rich repeats are found in extracellular proteins and chordin contains such repeats at the both termini, the presence of these structural motifs supports the view that chordin is a secreted protein.

Outside of the cys-rich repeats, the rest (681 amino acids) of the chordin protein does not have significant homology to any sequences in the databases. Therefore, chordin mRNA encodes a novel putative secreted protein. Because chordin is specifically expressed in regions of the embryo that have organizer activity, we also tested whether this molecule is active in inductive signalling.

For phenotypic analysis, the chordin cDNA was subcloned into an expression vector (Amaya et al., Cell, 66, pp. 257–270, 1991) and RNA synthesized with SP6 polymerase was injected into a single blastomere of Xenopus embryos. As shown in Table 1, chordin mRNA induced secondary axes at substantial frequencies when injected into ventral-vegetal blastomeres. When injected into dorsal or animal (top) blastomeres, a high proportion of dorsalized embryos resulted. Embryos injected with a control mRNA encoding an unrelated secreted protein (human prolactin in the same vector) were unaffected.

Immunostaining with a notochord marker showed that this secondary axis contained a notochord and lacked anterior structures such as eyes and cement glands, but had auditory vesicles, implying that the axis extended anteriorly at least as far as the hindbrain. Of 37 twinned embryos (injected at the 8-cell stage) stained with this antibody, 64% had a notochord in the secondary axis and 54% had secondary auditory vesicles. In Xenopus, the absence of a differentiated notochord in experimentally manipulated embryos is not uncommon. Many axes were similar to those induced by ectopic expression of gsc or activin, but differences were also noted. In particular, embryos with double tails were found in 11% of the twinned embryos (n=223), suggesting that chordin can induce tail-organizing activity in some cases. Twinned embryos with duplicated anterior structures were observed at a low frequency (15% with double cement glands and 4.5% with extra eyes). On the other hand, enlarged head structures, such as cement glands, were commonly observed in dorsalized embryos caused by chordin mRNA injections into dorsal or animal blastomeres.

TABLE 1

Microinjection of Chordin mRNA Into Early Xenopus Embryos Produces Twinned and Dorsalized Embryos

| RNA | Blastomer | Stage | # Without Phenotype | # with two axes | # with dorsalization |
| --- | --- | --- | --- | --- | --- |
| chordin | animal pole | 4 cell | 4 (27%) | 3 (20%) | 8 (53%) |
| | dorsal-vegetal | 8 cell | 8 (38%) | 3 (14%) | 10 (48%) |
| | ventral-vegetal | 8 cell | 11 (24%) | 27 (59%) | 8 (17%) |
| | ventral-vegetal | 16 cell | 8 (28%) | 19 (65%) | 2 (7%) |
| | A4 | 32 cell | 18 (53%) | 3 (9%) | 13 (38%) |
| | B4 | 32 cell | 13 (46%) | 6 (21%) | 9 (32%) |
| | C4 | 32 cell | 16 (43%) | 13 (35%) | 8 (21%) |
| | D4 | 32 cell | 12 (44%) | 10 (37%) | 5 (19%) |
| prolactin | ventral-vegetal | 8 cell | 19 (100%) | 0 (0%) | 0 (0%) |

To examine the fate adopted by injected and uninjected cells, single blastomeres were injected at the 32-cell stage with a mixture of chordin and β-galactosidase (lineage tracer) mRNAs. It appears that chordin mRNA has both long- and short-range effects. When chordin in mRNA was injected into the A4 blastomere, the injected cells remained in the ectoderm and did not contribute to the secondary axis. When a ventral-marginal blastomere, C4, was injected, almost all embryos with secondary axes displayed labeling in part of the secondary axis itself, suggesting that the chordin-injected cells had their fate changed into that of Spemann's organizer.

To further test whether chordin can cause cell fate changes, we microinjected blastomere D4, whose normal fate is to form endodermal tissue. The progeny of D4 cells injected with chordin mRNA can undergo a change in cell fate so that instead of remaining in the endoderm they form part of the secondary axis mesoderm. This is what is expected when a secondary Spemann organizer is formed. This change in cell fate was obtained in 43% (n=30) of embryos with secondary axes; in the rest the label was found in the endoderm and not in the induced axis. When the same D4 experiment was performed with noggin mRNA, secondary axes were formed but in every case (n=23) the injected cells were found in the endoderm.

These results may be interpreted as an indication that in this experiment noggin formed a secondary Nieuwkoop center, while chordin caused vegetal cells to form Spemann organizer tissue in some cases. Another interpretation of these data is that both factors have similar inducing activities but that noggin is more diffusible in the embryo. One observation perhaps supporting the second interpretation is that at high doses noggin mRNA, unlike chordin mRNA, has a strong tendency to radially dorsalize the entire embryo in D4 injections, instead of inducing secondary axes.

The results suggest that in some embryos chordin can produce secondary axes by changing the fate of the injected cells, inducing them to form part of Spemann's organizer. In other embryos, the chordin-injected cells do not contribute to the secondary axis at all, and may remain entirely in the endoderm of embryos injected into the D4 cell. These non-cell-autonomous effects of chordin are in agreement with the observation that it encodes a secreted protein, while the cell-autonomous effects on injected cells may be explained by autocrine and/or short-range paracrine mechanisms. We conclude that cells injected with chordin mRNA acquire axis-inducing activity and that they can recruit uninjected cells into secondary axes.

To further test the axis-forming activity of chordin a UV-rescue assay was used. This method is frequently favored in Xenopus embryology due to its high level of sensitivity. Ventralized embryos resulting from UV treatment, lack axial structures as indicated by a Dorso-Anterior Index, DAI, of 0.1. (In this scale, a DAI of 0 corresponds to embryos with no axis, and a value of 5 to a normal embryo). When 75 pg of synthetic chordin mRNA were injected into a single vegetal blastomere of UV-treated embryos at the 8-cell stage, substantial rescue of trunk and tail structures occurred, although the embryos still lacked the most anterior head structures (DAI=2.1). These phenotypes were similar to those observed in rescue experiments with gsc or activin mRNA. When 150 pg of chordin mRNA were injected, the entire axis was rescued (DAI=4.2), including eyes and cement glands. When the amount of chordin RNA was doubled, embryos with exaggerated dorso-anterior structures, such as multiple cement glands (indicated by arrowheads), resulted (DAI=6.2).

When UV-treated embryos were microinjected into a blastomere of the C-tier region with a mixture of chordin and β-galactosidase mRNAs as a lineage tracer, the labeled chordin-injected cells were located in the dorsal axis (n=19), usually in anterior regions, or in endodermal cells (n=5). Histological analysis showed that the injected cells contribute preferentially to dorsal tissues, i.e., notochord and somites. This implies that expression of chordin changes the fate of the injected cells into organizer-like tissue. Most of the dorsal axis, however, was recruited from uninjected cells, including most of the somite and all of the neural tissue. Some rescued axes, particularly at low chordin mRNA concentrations, lacked a notochord and the somites were fused. In such cases, the injected cells were found in the somite, principally in the midline underlying the neural tube, indicating that chordin can rescue axial structures even in the absence of notochord tissue.

Thus chordin mRNA can completely rescue axis formation in ventralized embryos. The injected cells preferentially give rise to organizer derivatives and are able to recruit neighboring cells to form multiple dorsal tissues, including notochord.

We tested whether chordin can dorsalize mesoderm induced by bFGF. When animal caps were injected with either control prolactin or chordin mRNA and treated with bFGF, the control caps formed ventral mesoderm (blood and mesothelium), while chordin-injected caps formed dorsal mesoderm (notochord and muscle) as well as dorso-anterior ectodermal inductions such as cement glands and blocks of neural tissue. We conclude that chordin mRNA is able to synergize with bFGF, leading to the dorsalization of ventral mesoderm.

Synthetic chordin or control prolactin mRNA were microinjected into a single blastomere of embryos with clear dorso-ventral polarity. The amount of injected RNA was 150 pg for 16–32 cell embryos or 200 pg for 4–8 cell embryos. Combined results from two experiments are summarized here. Ten independent experiments were performed, and all gave similar results. Secondary axes were scored morphologically and include partial axes lacking anterior structures, complete axes and embryos with double tailbuds. Dorsalized embryos corresponded at least to a DAI 7 according to the criteria of Kao and Elinson, *Dev. Biol.*, 127, pp. 64–77, (1988).

TABLE 2

Chordin RNA Dorsalizes Ventral Mesoderm

| Explant | RNA | bFGF | AtEp | Bl | Mst | Mus | Noto | Neur | (n) |
|---|---|---|---|---|---|---|---|---|---|
| AC | prolactin | – | 100% | 0% | 0% | 0% | 0% | 0% | (18) |
| AC | chordin | – | 100% | 0% | 0% | 0% | 0% | 0% | (20) |
| AC | prolactin | + | 16% | 52% | 72% | 4% | 0% | 0% | (25) |
| AC | chlordin | + | 2% | 2% | 4% | 31% | 40% | 70% | (48) |
| VMZ | prolactin | – | 0% | 85% | 95% | 15% | 0% | 0% | (20) |
| VMZ | chlordin | – | 0% | 5% | 19% | 57% | 52% | 38% | (21) |

Animal caps (AC) were explanted at stage 8, incubated with or without 50 ng/ml of bFGF in 0.3× MBS solution containing 0.1 mg/ml BSA for 2 hours, and cultured in 0.3× MBS for 2 days. Microinjection of chordin mRNA did not produce elongation of animal cap explants by itself, but did cause elongation of most of the explants in the presence of bFGF. Ventral marginal zones (VMZs) were excised at stage 10½ and the explants were cultured for 2 days. Microinjection of chordin mRNA caused extensive elongation of VMZs. In the animal cap experiments, 300 pg of synthetic chordin mRNA were injected radially into each of the four animal pole blastomeres at the 8-cell stage. In the VMZ experiments, 200 pg of chordin mRNA were injected radially into each of the four vegetal blastomeres of 8-cell embryos. In both experiments, explants were fixed when sibling embryos reached stage 42. All explants were stained in whole-mount with the MZ-15 antibody marker, scored for notochord, and then embedded in paraffin, sectioned and scored by histology. The frequency of each type of tissue in the explants is shown. The data indicate that chordin per se is not a mesoderm inducer but acts as a modifier (dorsalizer) of mesoderm differentiation. AtEp, atypical epidermis; B1, blood; Mst, mesothelium; Mus, skeletal muscle; Noto, notochord; Neur, neural tissue.

EXPERIMENTAL PROCEDURES

Embryo manipulation

UV treatment was performed 30 min after fertilization for 60 sec with an UVG-11 lamp (UV-Products Inc). LiCl treatment was carried out in 0.12M LiCl in 0.1× modified Barth solution (MBS, Gurdon, 1976) for 40 min starting at the 32 cell stage. For ventral marginal zone (VMZ) experiments, an explant comprising 60° of the VMZs opposite to the dorsal lip was excised from stage 10¼–10½ embryos and cultured in 0.3× MBS until the stage indicated. For animal cap assays, animal caps devoid of marginal zone cells were explanted at stage 8, and incubated in 0.3× MBS containing 0.1 mg/ml BSA with or without 50 ng/ml human basic FGF (Promega) for three hours and subsequently cultured in 0.3× MBS for two days. Histological sections of embryos and explants were carried out using Paraplast at 10μm thickness and stained with hematoxylin-eosine.

Differential screening

RNA was isolated from LiCl-treated or UV-treated Xenopus gastrula embryos at stage 10½ as described (Cho et al., 1991). The poly $A^+$ fraction was purified with oligo (dT) latex (QIAGEN) and used to synthesize first-strand cDNA. After alkaline lysis of template RNA, the single-stranded cDNA was hybridized with an 5-fold excess of biotin-labeled maternal RNA (8-cell stage) followed by addition of streptavidin and phenol extraction as described (Sive and St John, 1988). Single-stranded cDNA enriched in zygotic genes was recovered from the aqueous phase. After a second identical subtraction, the cDNA was labeled with [α-32P] dCTP by the random primer labeling method (Prime-It II kit, Stratagene) and was used as a probe (LiCl or UV probe).

$2.5 \times 10^4$ pfu of unamplified Xenopus dorsal lip cDNA (stage 10½) ZAP phage library (Blumberg et al., 1991) were plated and lifted onto two replica nitrocellulose filters. Duplicate filters were hybridized with the LiCl or UV probes. Those plaques that gave a much stronger signal with the LiCl probe than with the UV probe were taken as positive clones. Twenty-two clones were positive after the second purification. These clones were classified into six groups by cross-hybridization using dot blot analysis. Whole-mount in situ hybridization analyses were performed using the longest insert in each group as a probe.

From the differential screening three chordin cDNAs were isolated, the longest of which was 2.3 kb (clone #59). Preliminary sequencing, the size of mature transcript in Northern blots (about 4 kb) and the lack of biological activity of microinjected synthetic RNA indicated that these clones were not full-length. After re-screening the dorsal lip library with clone #59 as a probe, 44 additional chordin cDNAs were isolated, of which five contained 3.8 kb inserts which were full-length and showed biological activity. DNA sequencing (of clone pBluescript chd-F11) was carried out on both strands using Sequenase ver. 2 (UBS) and the data analyzed using the Wisconsin GCG program on a VAX computer.

In situ hybridization and immunohistochemistry

Whole-mount in situ hybridization was performed as described previously (Harland, 1991) except for the use of a new substrate for alkaline phosphatase (BM purple AP-substrate, Boehringer). Much better signals were obtained with this substrate than with the conventional BCIP/NBT. The probe was synthesized using T7 RNA polymerase in the presence of digoxygenin-UTP using as a template a partial chordin clone, clone #59 (in pBluescript SK-) linearized with EcoRI. The probes for gsc and Xnot2 RNA were prepared as described previously (Cho et al 1991; Gont et al 1993). A fragment spanning the coding region of noggin cDNA was obtained by RT-PCR using stage 11 Xenopus embryo mRNA as a template, and subcloned into the Hind III- Xba I site of pBluescript KS-. Sequencing analysis showed no base changes to the previously reported nucleotide sequence (Smith and Harland, 1992). The noggin antisense probe was synthesized with T7 polymerase using this plasmid linearized with Nco I (the Nco I site was introduced at the initial Met site by PCR).

Immunohistochemistry for notochord staining was carried out with MZ-15 antibody as described (Smith and Watts, 1985; Dent et al, 1989). In lineage tracing experiments, α-galactosidase activity was visualized using X-gal in a conventional method (Sanes et al., 1986) except that the reaction mixture was adjusted to pH 6.8.

Synthetic mRNAs

The protein coding regions of chordin and noggin were amplified by PCR and the amplified fragment was subcloned into pSP35T, an expression vector that contains an SP6 promoter and β-globin 5' leader and 3' trailer sequences as well as a polyadenylate tail (Amaya et al., 1991). These expression vectors were named pSP35-chd and pSP35-noggin, respectively.

mRNA was synthesized in vitro in the presence of cap analogue and GTP (ratio 5:1) using the Megascript kit (Ambion) from pSP35-chd linearized with Xba I or pSP35-noggin linearized with EcoRI as a template. The mRNAs for gsc, Xnot and XlHbox 1 were synthesized as described previously (Niehrs et al., 1994; Gont et al., 1993; Wright et al., 1989). For control experiments, sense β-galactosidase RNA (from pCDM8-β-gal; Sasai et al 1992) or prolactin RNA (from pSP35T; Amaya et al., 1991) was injected. Microinjection into a Xenopus blastomeres was as described (Cho et al., 1991). In the case of noggin mRNA injection, 75 pg or less was used to induce secondary axes since we found that microinjection of more than 100 pg of noggin mRNA synthesized from this construct had a strong tendency to produce radially dorsalized embryos.

Activin treatment of animal cap explants and RNA blotting analysis

Activin and cycloheximide (CHX) treatments of animal cap explants were performed as described previously (Rosa, 1989; Cho et al., 1991). Animal caps were excised at stage 8, preincubated in 1× MBS with or without 5 μg/ml CHX for 30 min, and treated with 30 ng/ml recombinant human activin A (Genentech) for 150 min in the presence or absence of CHX. Total RNA was isolated from these explants and embryos of several early stages with RNA-STAT 60 kit (Tel-Test "B", Inc). Ten μg of total RNA was separated by formaldehyde agarose gel electrophoresis, transferred to Gene Screen Plus (Du Pont) and hybridized with full-length chordin, gsc or noggin probes in 5× SSPE, 1% SDS, 150 μg/ml heat-denatured salmon sperm DNA and 50% formamide at 42° C. as recommended by the manufacturer.

It is to be understood that while the invention has been described above in conjunction with preferred specific embodiments, the description and examples are intended to illustrate and not limit the scope of the invention, which is defined by the scope of the appended claims.

It is claimed:

1. An isolated DNA encoding a functional protein, and having the nucleotide sequence of SEQ ID NO:1.

2. An isolated DNA encoding a functional protein having the amino acid sequence of SEQ ID NO:2.

3. A construct comprising DNA of claim 1 or 2 operatively linked with an expression vector.

4. The construct as in claim 3 wherein the expression vector is mammalian, viral, bacterial, or baculoviral.

5. A transformant obtained by introducing the construct of claim 3 into a host.

6. The DNA as in claim 1 or 2 wherein the protein encoded thereby induces dorsal development in vertebrates.

7. The DNA as in claim 1 or 2 wherein the protein encoded thereby induces neural development in vertebrates.

8. The DNA as in claim 1 or 2 wherein the protein encoded thereby induces endodermal differentiation in vertebrates.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 3796 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| AGAAGTGTCC | CCTCCGGACA | TTGGTACCTG | CTGTGAAGAA | GAGGCTGGCC | CGGGTAGCAG | 60 |
| GGAGCGCTCT | CTGCACTATT | GGAGTGTGTG | TGGTGCAAAG | TGTGTGTACA | GAGCAACAAC | 120 |
| CCATGTACTG | GGAATGTGAG | CCAGAGAGCC | AGAGACAAGT | AGCATAGTAG | TCGCTGAGAA | 180 |
| GGTGGCAAAG | TGACTGGCAC | AGGCAGACTG | AAGGCTCATG | GTCCATAGAA | GAGTATAGTA | 240 |
| CAAAGCACAG | ACATTGTACG | CTCACTATAC | GAGACAGAAC | GTTGGAACC | ACAAAAATGC | 300 |
| AGTGTCCCCC | CATCCTACTT | GTGTGGACCC | TGTGGATTAT | GGCTGTGGAT | TGCTCTCGCC | 360 |
| CAAAGGTTTT | CTTGCCCATT | CAGCCTGAAC | AGGAGCCCCT | CCAATCCAAG | ACTCCAGCAG | 420 |
| GTTGTACATT | TGGTGGGAAA | TTTTACTCCC | TGGAGGATTC | ATGGCATCCA | GATCTTGGGG | 480 |
| AACCATTCGG | AGTTATGCAC | TGCGTACTAT | GCTATTGTGA | GCCGCAGCGA | AGTCGTCGGG | 540 |
| GAAAACCATC | TGGTAAAGTC | AGCTGCAAAA | ACATCAAACA | TGATTGCCCC | TCACCCTCCT | 600 |
| GTGCTAACCC | TATACTGCTC | CCATTACATT | GCTGCAAGAC | TTGTCCCAAA | GCTCCTCCTC | 660 |
| CTCCTATAAA | GAAATCAGAC | TTTGTTTTG | ACGGATTTGA | GTATTTCAA | GAGAAGGATG | 720 |
| ATGATCTTTA | TAATGATCGC | TCTTATCTGA | GTTCTGATGA | TGTCGCTGTG | GAGGAGAGTC | 780 |
| GTTCAGAATA | TGTGGCACTA | CTAACAGCAC | CCAGCCATGT | GTGGCCCCCA | GTTACCAGTG | 840 |
| GAGTAGCCAA | GGCTAGATTC | AACCTGCAGC | GCTCCAATTT | GCTCTTCTCA | ATCACTTATA | 900 |
| AATGGATAGA | CAGACTTTCC | AGAATCCGTT | TCTCCGATCT | TGACGGTTCT | GTGCTGTTTG | 960 |
| AACACCCAGT | GCACAGAATG | GGATCCCCAC | GGGATGACAC | TATCTGTGGC | ATTTGGAGGT | 1020 |
| CCCTTAATCG | GTCCACTCTA | CGTCTTCTCC | GAATGGGTCA | CATTCTTGTA | TCTCTGGTGA | 1080 |
| CCACAACACT | TTCAGAGCCG | GAAATATCAG | GCAAGATTGT | CAAACACAAA | GCCCTATTTT | 1140 |
| CAGAGTCCTT | CAGTGCACTT | CTTACCCCAG | AAGACTCTGA | TGAAACAGGA | GGTGGAGGAC | 1200 |
| TCGCAATGCT | AACACTGAGT | GATGTGGATG | ACAATCTGCA | CTTTATACTT | ATGCTCAGAG | 1260 |
| GTCTAAGTGG | TGAAGAAGGA | GATCAGATTC | CAATACTTGT | GCAAATCTCA | CATCAGAACC | 1320 |
| ATGTGATACG | GGAGCTATAT | GCCAACATCT | CTGCACAGGA | ACAAGACTTT | GCAGAGGTAT | 1380 |
| TGCCAGACCT | TTCCAGTCGA | GAAATGCTGT | GGCTGGCGCA | AGGTCAGCTG | GAGATTTCAG | 1440 |
| TGCAGACAGA | AGGGAGACGT | CCGCAAAGCA | TGTCAGGCAT | AATCACAGTC | AGAAAATCAT | 1500 |
| GTGACACTTT | GCAGAGTGTG | TTATCGGGTG | GTGACGCTTT | AAATCCCACC | AAAACTGGAG | 1560 |
| CCGTGGGATC | TGCAAGCATC | ACACTTCATG | AAAATGGAAC | TCTGGAATAT | CAGATTCAAA | 1620 |
| TTGCTGGTAC | AATGAGTACT | GTGACAGCTG | TGACACTGGA | GACAAACCT | CGCCGAAAAA | 1680 |
| CAAAGAGAAA | TATTCTGCAC | GATATGAGCA | AGGACTACCA | TGATGGAAGG | GTCTGGGGAT | 1740 |
| ATTGGATAGA | TGCTAATGCC | CGAGACCTAC | ATATGCTGTT | ACAAAGTGAG | CTCTTCCTCA | 1800 |

-continued

```
ATGTAGCGAC AAAGGACTTC CAGGAAGGGG AACTCAGGGG ACAAATAACC CCTCTGCTAT    1860
ACAGTGGCCT GTGGGCCAGA TATGAGAAGC TCCCAGTTCC TCTAGCTGGT CAGTTTGTGT    1920
CACCTCCCAT CAGGACAGGT TCAGCAGGTC ATGCATGGGT TTCACTGGAT GAGCACTGCC    1980
ACCTGCATTA TCAGATTGTG GTGACTGGTC TGGGTAAGGC AGAAGATGCT GCACTGAACG    2040
CACATCTACA TGGTTTTGCT GAGCTTGGAG AGGTCGGTGA GAGCTCTCCT GGACACAAGA    2100
GGTTGTTAAA GGGCTTCTAT GGGTCAGAGG CACAGGGTAG TGTAAAAGAC CTTGACCTTG    2160
AACTATTGGG ACATCTGAGC CGGGGCACAG CATTTATTCA AGTGAGCACC AAACTGAATC    2220
CTCGTGGGGA AATTCGAGGA CAGATACACA TACCTAACAG CTGTGAATCT GGAGGAGTTT    2280
CTCTAACCCC TGAAGAGCCT GAGTATGAAT ATGAAATATA TGAGGAGGGA AGGCAGCGCG    2340
ACCCTGACGA TCTTCGGAAA GACCCCAGAG CATGCTCTTT CGAAGGTCAA CTAAGGGCCC    2400
ATGGTTCACG ATGGGCTCCA GACTATGACA GGAAATGCTC TGTGTGCAGC TGTCAGAAGC    2460
GTACCGTGAT TTGTGATCCT ATTGTGTGCC CACCTCTGAA CTGCTCCCAG CCTGTCCATT    2520
TGCCAGATCA GTGCTGTCCT GTGTGTGAAG AAAAAAAGA AATGAGAGAG GTGAAAAAAC     2580
CAGAGAGGGC TCGCACAAGT GAAGGCTGCT TTTTGATGG AGATCGCTCA TGGAAGGCAG     2640
CTGGTACACG TTGGCATCCT TTTGTTCCTC CATTTGGTCT AATTAAATGT GCCATTTGCA    2700
CCTGCAAGGG TTCCACTGGA GAAGTGCACT GTGAGAAGGT GACCTGTCCA AAACTTTCCT    2760
GTACCAACCC AATCCGTGCC AATCCTTCTG ATTGCTGCAA GCAGTGCCCA GTAGAGGAGC    2820
GGAGTCCTAT GGAACTGGCA GACAGTATGC AGTCAGATGG AGCAGGATCA TGCAGATTTG    2880
GGCGTCACTG GTACCCAAAT CATGAGCGTT GGCATCCAAC TGTGCCACCC TTTGGAGAGA    2940
TGAAATGTGT TACATGCACT TGTGCGGAGG GCATTACACA GTGTCGGAGA CAGGAGTGTA    3000
CAGGAACTAC ATGTGGTACT GGTTCAAAGC GGGACAGATG TTGCACCAAG TGCAAAGATG    3060
CCAATCAAGA TGAAGATGAA AAAGTGAAAT CAGACGAGAC AAGGACTCCA TGGAGTTTTT    3120
AGAGAGGAGA GCAACTCGGG CAATGGGACT GATTATCTAG GCTCACAAAA ACATGTCCCA    3180
AGCTGAGACA ACTGCCAGGA CTGGATGGTC TGCACAATGT TTTGTTCCAC TCTGATAACA    3240
CTGCTACTGG ATTTTACAGT ATTTCCATTT GTTTCATTTG CTGCCATGAA GCAGTGGGAT    3300
TCTGGAGGCA GCATTTGGAA CTAAAATACC TTGCCACCTT GGATTCATCC CTTCCAACAC    3360
CAAGTCAGTC TTTCTGACAG AAGCAACTCT AAATCCTGCC TAAACAGGAC CCGGAGTTTT    3420
AACGTCTGAT CTGTAGAGTT TCGCAACAGG AGCACAGACA CAGCATAGGC AGCTGTGCAT    3480
ATGTAGATAT ACTGACTAAA CGTGCCTTGT GGCTCTACAG GACGGGAAGA AAAGTGCAAG    3540
AGACAGACAA AGACTACAGT GTTCTTGCTG GAAAGTCTGT ATATATGTCT GCGTATGTGA    3600
GTGTGTGAAC GCATGATTTT ACTTTGGGGG TGTATGATCA GACATATATC AGTTCCTCTT    3660
GTCCAAGCAC ACACTTTTGG AAACTTTGTC TTGTATTATT TATGGTATTT TGAGTGGGTG    3720
CGGTACCTGT ACTAATTAAC TATTATTGAT GGTCGTATTT ATTGAACTAA AATAAACTGA    3780
AGACATTTTC CCAGTC                                                    3796
```

( 2 ) INFORMATION FOR SEQ ID NO:2:

( i ) SEQUENCE CHARACTERISTICS:
        ( A ) LENGTH: 941 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Gln Cys Pro Pro Ile Leu Leu Val Trp Thr Leu Trp Ile Met Ala
1               5                   10                  15
Val Asp Cys Ser Arg Pro Lys Val Phe Leu Pro Ile Gln Pro Glu Gln
            20              25              30
Glu Pro Leu Gln Ser Lys Thr Pro Ala Gly Cys Thr Phe Gly Gly Lys
        35              40              45
Phe Tyr Ser Leu Glu Asp Ser Trp His Pro Asp Leu Gly Glu Pro Phe
    50              55              60
Gly Val Met His Cys Val Leu Cys Tyr Cys Glu Pro Gln Arg Ser Arg
65              70              75                          80
Arg Gly Lys Pro Ser Gly Lys Val Ser Cys Lys Asn Ile Lys His Asp
            85              90                          95
Cys Pro Ser Pro Ser Cys Ala Asn Pro Ile Leu Leu Pro Leu His Cys
            100             105             110
Cys Lys Thr Cys Pro Lys Ala Pro Pro Pro Ile Lys Lys Ser Asp
            115             120             125
Phe Val Phe Asp Gly Phe Glu Tyr Phe Gln Glu Lys Asp Asp Asp Leu
    130             135             140
Tyr Asn Asp Arg Ser Tyr Leu Ser Ser Asp Val Ala Val Glu Glu
145             150             155             160
Ser Arg Ser Glu Tyr Val Ala Leu Leu Thr Ala Pro Ser His Val Trp
            165             170             175
Pro Pro Val Thr Ser Gly Val Ala Lys Ala Arg Phe Asn Leu Gln Arg
            180             185             190
Ser Asn Leu Leu Phe Ser Ile Thr Tyr Lys Trp Ile Asp Arg Leu Ser
            195             200             205
Arg Ile Arg Phe Ser Asp Leu Asp Gly Ser Val Leu Phe Glu His Pro
210             215             220
Val His Arg Met Gly Ser Pro Arg Asp Asp Thr Ile Cys Gly Ile Trp
225             230             235             240
Arg Ser Leu Asn Arg Ser Thr Leu Arg Leu Leu Arg Met Gly His Ile
            245             250             255
Leu Val Ser Leu Val Thr Thr Thr Leu Ser Glu Pro Glu Ile Ser Gly
            260             265             270
Lys Ile Val Lys His Lys Ala Leu Phe Ser Glu Ser Phe Ser Ala Leu
        275             280             285
Leu Thr Pro Glu Asp Ser Asp Glu Thr Gly Gly Gly Gly Leu Ala Met
        290             295             300
Leu Thr Leu Ser Asp Val Asp Asp Asn Leu His Phe Ile Leu Met Leu
305             310             315             320
Arg Gly Leu Ser Gly Glu Glu Gly Asp Gln Ile Pro Ile Leu Val Gln
            325             330             335
Ile Ser His Gln Asn His Val Ile Arg Glu Leu Tyr Ala Asn Ile Ser
            340             345             350
Ala Gln Glu Gln Asp Phe Ala Glu Val Leu Pro Asp Leu Ser Ser Arg
        355             360             365
Glu Met Leu Trp Leu Ala Gln Gly Gln Leu Glu Ile Ser Val Gln Thr
    370             375             380
Glu Gly Arg Arg Pro Gln Ser Met Ser Gly Ile Ile Thr Val Arg Lys
385             390             395             400
Ser Cys Asp Thr Leu Gln Ser Val Leu Ser Gly Gly Asp Ala Leu Asn
            405             410             415
Pro Thr Lys Thr Gly Ala Val Gly Ser Ala Ser Ile Thr Leu His Glu
```

-continued

```
                        420                        425                        430
Asn  Gly  Thr  Leu  Glu  Tyr  Gln  Ile  Gln  Ile  Ala  Gly  Thr  Met  Ser  Thr
               435                      440                      445
Val  Thr  Ala  Val  Thr  Leu  Glu  Thr  Lys  Pro  Arg  Arg  Lys  Thr  Lys  Arg
     450                      455                      460
Asn  Ile  Leu  His  Asp  Met  Ser  Lys  Asp  Tyr  His  Asp  Gly  Arg  Val  Trp
465                      470                      475                           480
Gly  Tyr  Trp  Ile  Asp  Ala  Asn  Ala  Arg  Asp  Leu  His  Met  Leu  Leu  Gln
                    485                      490                           495
Ser  Glu  Leu  Phe  Leu  Asn  Val  Ala  Thr  Lys  Asp  Phe  Gln  Glu  Gly  Glu
               500                      505                      510
Leu  Arg  Gly  Gln  Ile  Thr  Pro  Leu  Leu  Tyr  Ser  Gly  Leu  Trp  Ala  Arg
          515                      520                      525
Tyr  Glu  Lys  Leu  Pro  Val  Pro  Leu  Ala  Gly  Gln  Phe  Val  Ser  Pro  Pro
     530                      535                      540
Ile  Arg  Thr  Gly  Ser  Ala  Gly  His  Ala  Trp  Val  Ser  Leu  Asp  Glu  His
545                      550                      555                           560
Cys  His  Leu  His  Tyr  Gln  Ile  Val  Val  Thr  Gly  Leu  Gly  Lys  Ala  Glu
                    565                      570                           575
Asp  Ala  Ala  Leu  Asn  Ala  His  Leu  His  Gly  Phe  Ala  Glu  Leu  Gly  Glu
               580                      585                      590
Val  Gly  Glu  Ser  Ser  Pro  Gly  His  Lys  Arg  Leu  Leu  Lys  Gly  Phe  Tyr
          595                      600                      605
Gly  Ser  Glu  Ala  Gln  Gly  Ser  Val  Lys  Asp  Leu  Asp  Leu  Glu  Leu  Leu
     610                      615                      620
Gly  His  Leu  Ser  Arg  Gly  Thr  Ala  Phe  Ile  Gln  Val  Ser  Thr  Lys  Leu
625                      630                      635                           640
Asn  Pro  Arg  Gly  Glu  Ile  Arg  Gly  Gln  Ile  His  Ile  Pro  Asn  Ser  Cys
                    645                      650                           655
Glu  Ser  Gly  Gly  Val  Ser  Leu  Thr  Pro  Glu  Glu  Pro  Glu  Tyr  Glu  Tyr
               660                      665                      670
Glu  Ile  Tyr  Glu  Glu  Gly  Arg  Gln  Arg  Asp  Pro  Asp  Leu  Arg  Lys
          675                      680                      685
Asp  Pro  Arg  Ala  Cys  Ser  Phe  Glu  Gly  Gln  Leu  Arg  Ala  His  Gly  Ser
     690                      695                      700
Arg  Trp  Ala  Pro  Asp  Tyr  Asp  Arg  Lys  Cys  Ser  Val  Cys  Ser  Cys  Gln
705                      710                      715                           720
Lys  Arg  Thr  Val  Ile  Cys  Asp  Pro  Ile  Val  Cys  Pro  Pro  Leu  Asn  Cys
                    725                      730                           735
Ser  Gln  Pro  Val  His  Leu  Pro  Asp  Gln  Cys  Cys  Pro  Val  Cys  Glu  Glu
               740                      745                      750
Lys  Lys  Glu  Met  Arg  Glu  Val  Lys  Lys  Pro  Glu  Arg  Ala  Arg  Thr  Ser
          755                      760                      765
Glu  Gly  Cys  Phe  Phe  Asp  Gly  Asp  Arg  Ser  Trp  Lys  Ala  Ala  Gly  Thr
     770                      775                      780
Arg  Trp  His  Pro  Phe  Val  Pro  Pro  Phe  Gly  Leu  Ile  Lys  Cys  Ala  Ile
785                      790                      795                           800
Cys  Thr  Cys  Lys  Gly  Ser  Thr  Gly  Glu  Val  His  Cys  Glu  Lys  Val  Thr
                    805                      810                           815
Cys  Pro  Lys  Leu  Ser  Thr  Asn  Pro  Ile  Arg  Ala  Asn  Pro  Ser  Asp
               820                      825                      830
Cys  Cys  Lys  Gln  Cys  Pro  Val  Glu  Glu  Arg  Ser  Pro  Met  Glu  Leu  Ala
          835                      840                      845
```

| | | | | | | | | | | | | | | |
|---|---|---|---|---|---|---|---|---|---|---|---|---|---|---|
| Asp | Ser 850 | Met | Gln | Ser | Asp | Gly 855 | Ala | Gly | Ser | Cys | Arg 860 | Phe | Gly | Arg | His |
| Trp 865 | Tyr | Pro | Asn | His | Glu 870 | Arg | Trp | His | Pro | Thr 875 | Val | Pro | Pro | Phe | Gly 880 |
| Glu | Met | Lys | Cys | Val 885 | Thr | Cys | Thr | Cys | Ala 890 | Glu | Gly | Ile | Thr | Gln 895 | Cys |
| Arg | Arg | Gln | Glu 900 | Cys | Thr | Gly | Thr | Thr 905 | Cys | Gly | Thr | Gly | Ser 910 | Lys | Arg |
| Asp | Arg | Cys 915 | Cys | Thr | Lys | Cys | Lys 920 | Asp | Ala | Asn | Gln | Asp 925 | Glu | Asp | Glu |
| Lys | Val 930 | Lys | Ser | Asp | Glu | Thr 935 | Arg | Thr | Pro | Trp | Ser 940 | Phe | | | |

( 2 ) INFORMATION FOR SEQ ID NO:3:

( i ) SEQUENCE CHARACTERISTICS:
( A ) LENGTH: 340 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

```
GGCCAACACC  TCCGCTCAGG  AGCCAGGTTT  TGCTGAGGTG  CTGCCCAGCC  TTACAGACCA    60
AGAGATGGAC  TGGTTGGAGC  TGGGGGAGCT  GCAGATGGTC  CTAGAGAAGG  CGGGTGGGCC   120
AGAGCTACGC  ATCAGTGGAT  ACATCACCAC  CAGGNAGAGC  TGTGATGTCC  TTCAAAGTGT   180
CCTNTGTGGT  GGTGATGCCC  TGATCCCAGT  CCAGACGGGT  GCTGCTGGAT  CAGACAGCTT   240
CATATTGNTA  GGAAATGGCT  CCCTTATCTA  TCAGGTACAA  GTGGTAGGTA  CAGGTAGCGA   300
GGTGGTGGCC  ATAACACTGG  AGACCAACCC  TCAGGGGAAG                          340
```